US008853263B2

(12) United States Patent
Smith-Swintosky et al.

(10) Patent No.: US 8,853,263 B2
(45) Date of Patent: *Oct. 7, 2014

(54) CO-THERAPY FOR THE TREATMENT OF EPILEPSY AND RELATED DISORDERS

(75) Inventors: Virginia L. Smith-Swintosky, Hatfield, PA (US); David F. McComsey, Warminster, PA (US); Michael H. Parker, Chalfont, PA (US); Allen B. Reitz, Lansdale, PA (US); Bruce E. Maryanoff, Forest Grove, PA (US)

(73) Assignee: Janssen Pharmaceutica NV, Beerse (BE)

( * ) Notice: Subject to any disclaimer, the term of this patent is extended or adjusted under 35 U.S.C. 154(b) by 713 days.

This patent is subject to a terminal disclaimer.

(21) Appl. No.: 11/750,600

(22) Filed: May 18, 2007

(65) Prior Publication Data

US 2007/0293440 A1 Dec. 20, 2007

Related U.S. Application Data

(60) Provisional application No. 60/802,000, filed on May 19, 2006.

(51) Int. Cl.
*C07D 311/58* (2006.01)
*C07D 317/46* (2006.01)
*C07D 317/70* (2006.01)
*C07D 319/20* (2006.01)
*C07D 319/22* (2006.01)
*C07D 321/10* (2006.01)
*A61K 31/337* (2006.01)
*A61K 31/18* (2006.01)
*A61K 45/06* (2006.01)

(52) U.S. Cl.
CPC ............ *A61K 31/337* (2013.01); *C07D 321/10* (2013.01); *C07D 317/70* (2013.01); *C07D 317/46* (2013.01); *C07D 311/58* (2013.01); *C07D 319/22* (2013.01); *C07D 319/20* (2013.01); *A61K 31/18* (2013.01); *A61K 45/06* (2013.01)
USPC ........... 514/463; 514/465; 514/454; 514/456; 514/452; 514/450; 549/349; 549/350; 549/359; 549/365; 549/407

(58) Field of Classification Search
USPC .................................. 514/183, 450, 456, 466
See application file for complete search history.

(56) References Cited

U.S. PATENT DOCUMENTS

| | | | |
|---|---|---|---|
| 2,527,861 A | 10/1950 | Walter | |
| 3,143,549 A | 8/1964 | Lafferty et al. | |
| 3,318,952 A | 5/1967 | Houlihan | |
| 3,383,414 A | 5/1968 | Houlihan | |
| 3,539,573 A | 11/1970 | Schmutz | |
| 3,621,096 A | 11/1971 | Prange et al. | |
| 4,513,006 A | 4/1985 | Maryanoff et al. | |
| 4,539,413 A | 9/1985 | Mouzin et al. | |
| 4,710,500 A | 12/1987 | Perregaard | |
| 4,804,663 A | 2/1989 | Kennis et al. | |
| 4,831,031 A | 5/1989 | Lowe, III et al. | |
| 4,879,288 A | 11/1989 | Warawa et al. | |
| 5,112,838 A | 5/1992 | Perregaard et al. | |
| 5,158,952 A | 10/1992 | Janssen et al. | |
| 5,192,785 A | 3/1993 | Lo et al. | |
| 5,194,446 A | 3/1993 | Lo et al. | |
| 5,212,326 A | 5/1993 | Meade | |
| 5,229,382 A | 7/1993 | Chakrabarti et al. | |
| 5,238,945 A | 8/1993 | Perregaard et al. | |
| 5,242,942 A | 9/1993 | Costanzo et al. | |
| 5,258,402 A | 11/1993 | Maryanoff | |
| 5,273,993 A | 12/1993 | Lo et al. | |
| 5,312,925 A | 5/1994 | Allen et al. | |
| 5,384,327 A | 1/1995 | Costanzo et al. | |
| 5,387,700 A | 2/1995 | Maryanoff et al. | |
| 5,731,348 A | 3/1998 | Gu et al. | |
| 5,753,693 A | 5/1998 | Shank | |
| 5,753,694 A | 5/1998 | Shank | |
| 5,760,007 A | 6/1998 | Shank et al. | |
| 5,780,650 A | 7/1998 | Furukawa et al. | |
| 5,935,933 A | 8/1999 | Shank et al. | |
| 5,998,380 A | 12/1999 | Ehrenberg et al. | |
| 6,071,537 A | 6/2000 | Shank | |
| 6,150,419 A | 11/2000 | Fairbanks et al. | |
| 6,187,338 B1 | 2/2001 | Caruso et al. | |
| 6,191,163 B1 | 2/2001 | Cottrell | |
| 6,211,241 B1 | 4/2001 | Islam et al. | |
| 6,319,903 B1 | 11/2001 | Carrazana et al. | |
| 6,322,503 B1 | 11/2001 | Sparhawk, Jr. | |

(Continued)

FOREIGN PATENT DOCUMENTS

CA 2 416 647 A 1/2003
DE 1211166 2/1966

(Continued)

OTHER PUBLICATIONS

Drug Facts and Comparison (1995 Edition, pp. 1607).*
New England Journal of Medicine, vol. 342:505-507, 2001.*
Merck Manuals Online Medical Library, www.merck.com, 2007).*
Cleeves et al., "Trazodone is ineffective in essential tremor", J. Neurol Nerusurg Psychiatry, 1990, 53:268-269.*
Robinson et al. "Pregablin not Effective for Essential Tremor", www.medpagetoday.com, 2009.*
Koller et al., "Essential Tremor Variants: Effect of Treatment", abstract, Clinical Pharmacology, 1987.*
CA 835894-69-4 Sulfamide (1,3-benzodioxol-2-ylmethyl).
CA Plus 835894-67-2 Sulfamic acid (1,3-benzodioxol-2-ylmethyl ester).

(Continued)

*Primary Examiner* — Eric Olson
(74) *Attorney, Agent, or Firm* — Hal B. Woodrow

(57) ABSTRACT

The present invention is directed to co-therapy for the treatment of epilepsy and related disorders comprising administering to a subject in need thereof, co-therapy with a therapeutically effective amount of a benzo-fused heterocycle sulfamide derivative and a therapeutically effective amount of one or more anticonvulsant and/or anti-epileptic agents.

17 Claims, No Drawings

(56) References Cited

U.S. PATENT DOCUMENTS

| | | | |
|---|---|---|---|
| 6,323,236 B2 | 11/2001 | McElroy | |
| 6,391,877 B1 | 5/2002 | Islam et al. | |
| 6,503,884 B1 | 1/2003 | Ehrenberg et al. | |
| 6,559,293 B1 | 5/2003 | Almarsson et al. | |
| 6,562,865 B1 | 5/2003 | Codd et al. | |
| 6,583,172 B1 | 6/2003 | Shank | |
| 6,627,653 B2 | 9/2003 | Plata-Salaman et al. | |
| 6,852,701 B2 | 2/2005 | Plata-Salaman et al. | |
| 6,852,738 B2 | 2/2005 | Jones et al. | |
| 6,949,518 B1 | 9/2005 | Chu | |
| 2001/0008889 A1 | 7/2001 | Caruso et al. | |
| 2002/0015713 A1 | 2/2002 | Murdock et al. | |
| 2004/0073037 A1 | 4/2004 | Jones et al. | |
| 2004/0192690 A1 | 9/2004 | Buxton et al. | |
| 2004/0253223 A1 | 12/2004 | Rodriguez | |
| 2005/0148603 A1 | 7/2005 | Jimenez et al. | |
| 2005/0282887 A1 | 12/2005 | McComsey et al. | |
| 2006/0047001 A1 | 3/2006 | Parker et al. | |
| 2006/0241172 A1 | 10/2006 | Zhou et al. | |
| 2006/0270856 A1 | 11/2006 | Abdel-Magid et al. | |
| 2006/0276528 A1 | 12/2006 | Abdel-Magid et al. | |
| 2007/0155823 A1* | 7/2007 | Smith-Swintosky et al. | 514/450 |
| 2007/0155824 A1* | 7/2007 | Smith-Swintosky | 514/450 |
| 2007/0155826 A1* | 7/2007 | Smith-Swintosky et al. | 514/450 |
| 2007/0293476 A1 | 12/2007 | Smith-Swintosky et al. | |
| 2009/0138544 A1* | 5/2009 | Wegenkittl et al. | 709/203 |
| 2009/0182141 A1 | 7/2009 | Abdel-Magid et al. | |
| 2009/0209634 A1* | 8/2009 | Smith-Swintosky | 514/452 |
| 2009/0247617 A1 | 10/2009 | Abdel-Magid et al. | |
| 2009/0247618 A1 | 10/2009 | Ballentine et al. | |
| 2009/0318544 A1 | 12/2009 | Mehrman et al. | |
| 2010/0063138 A1 | 3/2010 | McComsey et al. | |

FOREIGN PATENT DOCUMENTS

| | | |
|---|---|---|
| DE | 2022370 | 12/1971 |
| DK | 9800727 A | 5/1998 |
| EP | 0138441 B1 | 4/1985 |
| EP | 0483881 B1 | 5/1992 |
| EP | 490689 | 6/1992 |
| EP | 498770 | 8/1992 |
| EP | 503440 A1 | 9/1992 |
| EP | 478954 | 10/2000 |
| EP | 1056733 | 12/2000 |
| EP | 1118610 | 7/2001 |
| GB | 1087602 | 10/1967 |
| GB | 1111706 | 5/1968 |
| RU | 2246727 | 4/2004 |
| RU | 2226357 | 8/2004 |
| WO | WO 94/14827 A1 | 7/1994 |
| WO | WO 95/17406 A1 | 6/1995 |
| WO | 96/06822 A1 | 3/1996 |
| WO | WO 97/13510 A1 | 4/1997 |
| WO | 97/19919 | 6/1997 |
| WO | WO 97/19682 A1 | 6/1997 |
| WO | 97/35584 A1 | 10/1997 |
| WO | 98/00130 A2 | 1/1998 |
| WO | WO 98/00123 A1 | 1/1998 |
| WO | WO 98/00124 A1 | 1/1998 |
| WO | WO 98/00131 A1 | 1/1998 |
| WO | 98/06708 A1 | 2/1998 |
| WO | 98/07447 A1 | 2/1998 |
| WO | 98/15270 | 4/1998 |
| WO | 99/44581 A2 | 9/1999 |
| WO | 99/62522 | 12/1999 |
| WO | WO 00/01376 A2 | 1/2000 |
| WO | 00/07583 A2 | 2/2000 |
| WO | 00/42995 A2 | 7/2000 |
| WO | 00/42996 A2 | 7/2000 |
| WO | 00/49017 | 8/2000 |
| WO | WO 00/50020 A2 | 8/2000 |
| WO | 00/54588 A1 | 9/2000 |
| WO | 00/61137 | 10/2000 |
| WO | 00/61139 A1 | 10/2000 |
| WO | 00/61140 A1 | 10/2000 |
| WO | 00/66109 A2 | 11/2000 |
| WO | 00/76493 A1 | 12/2000 |
| WO | 01/13904 A2 | 3/2001 |
| WO | 01/76576 A2 | 10/2001 |
| WO | 02/03984 | 1/2002 |
| WO | WO 02/07821 A | 1/2002 |
| WO | 02/09694 | 2/2002 |
| WO | 02/30881 | 4/2002 |
| WO | 02/089785 | 11/2002 |
| WO | WO 02/096424 A1 | 12/2002 |
| WO | WO 2004/014352 | 2/2004 |
| WO | WO 2004/093912 A1 | 4/2004 |
| WO | WO 2004/092116 A1 | 10/2004 |
| WO | WO 2004/096771 A1 | 11/2004 |
| WO | WO 2004/098584 A1 | 11/2004 |
| WO | WO 2005/020917 A2 | 3/2005 |
| WO | WO 2006/007435 | 1/2006 |
| WO | WO 2006/007436 | 1/2006 |
| WO | WO 2006/010008 A1 | 1/2006 |
| WO | WO 2006/010750 A1 | 2/2006 |
| WO | WO 2006/023861 A1 | 3/2006 |
| WO | 2006/127184 | 11/2006 |
| WO | 2007/075695 | 7/2007 |
| WO | 2007/075698 | 7/2007 |
| WO | 2007/075717 | 7/2007 |
| WO | 2007/075751 | 7/2007 |
| WO | 2007/075752 | 7/2007 |
| WO | 2007/075833 | 7/2007 |
| WO | WO 2007/075834 | 7/2007 |
| WO | 2007/092086 | 8/2007 |
| WO | 2007/095615 | 8/2007 |
| WO | 2007/095618 | 8/2007 |
| WO | 2007/098486 | 8/2007 |
| WO | 2007/137167 | 11/2007 |
| WO | 2009/089210 | 7/2009 |
| WO | 2009/120191 | 10/2009 |
| WO | 2009/120192 | 10/2009 |

OTHER PUBLICATIONS

CA Plus 835894-65-0 Sulfamide [(3, 4-dihydro-2H-1-benzopyran-2-yl) methyl].

CA Plus 835894-63-8 Sulfamic acid (3,4-dihydro-2H-1-benzopyran-2-yl)methyl ester.

Stoll et al., Harvard Rev. Psychiatry, Jul./Aug. 1996, vol. 4, No. 2, 77-89.

Rygula et al., "Anhedonia and motivational deficits in rats: Impact of chronic social stress", Behavioral Brain Research, 162 (2005) 127-134.

Tenovuo, O. "Central Acetylcholinesterase Inhibitors in the Treatment of Chronic Traumatic brain Injury-Clinical Experience in 111 Patients". Progress in Neuro-Psychopharmacology and Biological Psychiatry 2005 US, vol. 29, No. 1, Jan. 2005, pp. 61067. XP002431412.

Shank, R.P., et al., "Examination of Two Independent Kinetic Assays for Determining the Inhibition of Carbonic Anhydrases aI and II: Structure-Activity Comparision of Sulfamataes and Sulfamides". Chemical Biology and Drug Design 2006, UK, vol. 68, No. 2, 2006, pp. 113-119. X002431414.

Klinger, A.L., et al. "Inhibition of Carbonic Anhydrase-II by Sulfamate and Sulfamide Groups: An Investigation Involving Direct Thermodynamic Binding Measurements", Journal of Medicinal Chemistry, Jun. 15, 2006, US, vol. 49, No. 12, pp. 3496-3500. XP002431415.

Waugh, J. et al. "Topiramate: As Monotherapy in Newly Diagnosed Epilepsy" CNS Drugs 2003 New Zealand, vol. 17, No. 13, 2003 pp. 985-992. XP009083685.

Guillaume, D. et al. "GIaI Contribution to Seizure: Carbonic Anhydrase Activity in Epileptic Marnmalian Brain" Epilepsia 1991 U.S., vol. 32, No. 1, 1991, pp. 10-15. XP009083684.

U.S. Appl. No. 11/154,443, Maryanoff Bruce E.
U.S. Appl. No. 11/154,386, McComsey David F.
U.S. Appl. No. 11/209,122, Maryanoff Bruce E.
U.S. Appl. No. 11/611,938, Smith-Swintosky.
U.S. Appl. No. 11/611,961, Reitz Allen B.

(56) References Cited

OTHER PUBLICATIONS

U.S. Appl. No. 11/612,071, Reitz Allen B.
U.S. Appl. No. 11/612,146, Smith-Swintosky.
U.S. Appl. No. 11/612,202, Reitz Allen B.
U.S. Appl. No. 11/612,222, Smith-Swintosky.
U.S. Appl. No. 11/612,249, Reitz Allen B.
U.S. Appl. No. 11/673,705, Smith-Swintosky.
U.S. Appl. No. 11/673,709, Smith-Swintosky.
U.S. Appl. No. 11/673,713, Smith-Swintosky.
U.S. Appl. No. 11/673,723, Smith-Swintosky.
U.S. Appl. No. 11/673,977, Smith-Swintosky.
U.S. Appl. No. 11/673,987, Smith-Swintosky.
U.S. Appl. No. 11/673,998, Smith-Swintosky.
U.S. Appl. No. 11/674,011, Smith-Swintosky.
U.S. Appl. No. 11/674,021, Smith-Swintosky.
U.S. Appl. No. 11/677,717, Fawzy Nagy.
U.S. Appl. No. 60/883,442, Smith-Swintosky.
U.S. Appl. No. 11/612,174, Smith-Swintosky.
Aeberli, P. et al. "Neuropharmacological Investigation of N-Benzylsulfamides", Journal of Medicinal Chemistry, Jul. 1967, vol. 10, No. 4, pp. 636-642.
Ambrosini, P.J., Psychiatr. Serv. 2000, 51, 627-633.
American Diabetes Association, "Definition and Description of Diabetes Mellitus", Diabetes Care, Jan. 2006; p. S43-S48, vol. 29 Supplement 1.
Ananth, J., Psychother. Psychosom. 1998, 67, 61-70.
Ayata et al., "Suppression of cortical Spreading Depression in Migraine Prophylaxis", Ann Neurol 2006; 59:652-661.
Barry et al. Current status of the utilization of antiepipleptic treatmetns in mood, anxiety and aggression: drugs and devices, Jan. 2004, 35, 1.
Beck-Nielsen H., "In Vivo Glucose Metabolism, Insulin Secretion and, Insulin Action in Europids with Non-insulin-dependent Diabetes Mellitus (NIDDM) and Their First-degree Relatives", Diabet Med Sep. 1996;13(9 Suppl 6):S78-84.
Berman, R.M. et al., Depress. Anxiety 1997, 5, 154-164.
Besag et al. "Behavioural Effects of the New Anticonvulsants" Drug Safety, ADIS Press, Auckland, NZ, vol. 24, No. 7, 2001, pp. 513-536.
Breslau et al., "The impact of migraine. Epidemiology, risk factors, and co-morbidities" Neurology, 2001;56:S4-S12 (Abstract only).
Burton et al. Anti-epileptic drugs for pain management. Pain, Symptom, Control and Palliative Care, 2001, vol. 1, No. 2.
Cadieux, R.J., Am. Fam. Physician 1998, 58, 2059-2062.
Calabrese, J.R. et al., Eur. Neuropsychopharmacol. 1999, 9, S109-S112.
Calabresi et al., "Antiepileptic drugs in migraine: from clinical aspects to cellular mechanisms", TRENDS in Pharmacological Sciences, vol. 28, No. 4, 188-195 (2007).
Caumo A., "Insulin Sensitivity from Meal Tolerance Tests in Normal Subjects: A Minimal Model Index", J Clin Endocrinol Metab, 85(11):4396-402 2000.
Cavaletti G et al: "Experimental peripheral neuropathy induced in adult rats by repeated intraperitoneal administration of Taxal", Exper Neurol 133:64-72, 1995.
Chaplan SR et al: "Quantitative assessment of tactile allodynia in the rat paw". J Neurosci Meth, 53:55-63, 1994.
Crooke et al, Abstract, Topiramate Improves Glycemic Control Independent of Weight Loss in ob/ob Mice.diabetes. A Journal of the American Diabetes Association, Abstract Book 61st Scientific Sessions Friday, Jun. 22-Tuesday Jun. 26, 2001, 2158-PO, A513.
Demarest et al, Abstract, Topiramate Improves Glucose Tolerance and May Improve Insulin Sensitivity in Animal Models of Type 2 Diabetes Mellitus, diabetes, A Journal of the American Diabetes Association, Abstract Book 61st Scientific Sessions Friday, Jun. 22-Tuesday Jun. 26, 2001, 1254-P, A302.
Diamond et al, "Practical Approaches to Migraine Management", 2002, CNS Drugs, 16(6), pp. 385-403.
Dickenson et al. Neurobiology of neuropathic pain: mode of action of anticonvulsants. European Journal of Pain, 2002, 6 (Suppl. A): 51-60, 2002.

Dinneen S.F., "The Postprandial State: Mechanism of Glucose Intolerance", Diabet Med Aug. 1997;14 Suppl 3:S19-24.
Drach, B.S. et al.: "N-1,2,2,2,-tetra-chloroethyl-N',N'-dimethylsulphamide". Journal of Organic Chemistry of the USSR., vol. 13, No. 7, Jul. 1977, pp. 1289-1294, XP008067470.
Dressler et al., Benzodiazepine in geriatric patients . . . , Abstract, Anaesthesiologie und reanimation, 1996, vol. 21/5, pp. 136-138.
Dursun, S.M. et al., "Accelerated weight loss after treating refractory depression with fluoxetine plus topiramate: possible mechanisms of action?", The Canadian Journal of Psychiatry, vol. 46, No. 3, pp. 287-288, 2001.
Edwards, K.R. et al, Efficacy and safety of topiramate in the treatment of painful diabetic neuropathy: a double-blind placebo-controlled study ADIS Title: Topiramate: therapeutic use: Neurogenic pain; In patients with diabetic neuropathy: Neurology 54 (Suppl. 3): 81 Apr. 11, 2000.
Edwards, KR; Glantz, MJ; Button, J et al, Evaluation of Topiramate in the Management of Painful Diabetic Neuropathy. Presented at: 18th Annual Meeting of the American Pain Society; 1998, Fort Lauderdale, FL.
Emancipator K., "Laboratory Diagnosis and Monitoring of Diabetes Mellitus", Am J Clin Pathol, 112(5):665-74 1999.
Erfurth, Andreas et al., "Bupropion as add-on strategy in difficult-to-treat bipolar depressive patients", Neuropsychobiology, vol. 45, No. Sup 1, pp. 33-36, 2002.
Fakhoury et al., Epilepsy Behav. Aug. 2007, abstract.
Flatters, SJL et al: "Acetyl-L-carnitine prevents and reduces paclitaxel-induced painful peripheralneuropathy", Neurosci Lett 397:219-223, 2006.
Gareri, P. et al, Progress in Neurobiology 61, 2000, 353-396.
Garonna, F. et al., "Topiramate in the treatment of overweight/obese binge eaters ADIS Title: Topiramate: therapeutic use; Obseity; in patient with binge eating disorders" International Journal of Neuropsychopharmacology 3(Suppl 1): 299: Jul. 2000 XP001030426 Bassano dG Vicenza Italy, whole document.
Goldberg R.G., "Prevention of Type 2 Diabetes", Med Clin North Am, Jul. 1998;82(4):805-21.
Gorelick D A, "Pharmacological treatment" Recent Developments in Alcoholism, vol. 11, 1993, p. 413-427, XP00913482 p. 417.
Gorelick et al., Drugs 2004: 64(14), pp. 1547-1573.
Grond et al., "Weak Opioids—an educational substitute for morphine?", Current Opinion in Anaesthesiology, vol. 11, No. 5, 1998, pp. 559-565 XP00982759.
Groop L., "Characterization of the Prediabetic State", Am J Hypertension; Sep. 1997;10(9 Pt 2):172S-180S.
Haffner S.M., "Impaired Glucose Tolerance, Insulin Resistance and Cardiovascular Disease", Diabetic Medicine, Aug. 1977;14 Suppl 3:S12-8.
Haffner S.M., "The Prediabetic Problem: Development of Non-Insulin-Dependent Diabetes Mellitus and Related Abnormalities", J Diabetes Complications, Mar.-Apr. 1997; 11(2):69-76.
Harrison's Principles of Internal Medicine, Isselbacher et al. eds. McGraw-Hill, Inc., New York, 1994, p. 69.
Hatzinger, M. et al., Wien. Med. Wochenschr. 1999, 149, 511-514.
Hauner H, "Managing type 2 diabetes mellitus in patients with obesity," Treatments in Endocrinology, 2004, 3(4), 223-232 (only abstract provided).
Headache Classification Committee of the International Headache Society. Cephalalgia 1988;8 Suppl 7:1-96.
Hering et al., "Sodium valproate in the treatment of cluster headache", Cephalalgia (Sep. 1989) 9(3) pp. 195-198.
Huisman, M. et al.: "Synthesis of N-(diemthylsulphamoyl)aldimines, a new type of aldimine derivative". Synthetic Communications, vol. 27, No. 6, 1997, pp. 945-952.
Jay et al., "Epilepsy, Migraine and EEG Abnormalities in Children: a Review & Hypothesis," Journal of Head and Face Pain, abstract, vol. 22, Issue 3, pp. 110-114, 1982.
Johnson, SA CNS Drugs, 2005. vol. 19, No. 10, pp. 873-896.
Johnson, B A: "Progress in the development of topiramate for treating alcohol dependence: From a hypothesis to a proof-of-concept study" Alcoholism: Clinical and Experimental Research 2004 United States, vol. 28, No. 8, 2004, pp. 1137-1144.

(56) References Cited

OTHER PUBLICATIONS

Kawasaki, "Structural and functional analysis of pancreatic islets preserved by pioglitazone in db/db mice", Am J Physiol Endocrinol Metab; 2004, p. E510-E518, doi 10.1152/ajpendo.00128.2004.
Kent, J.M., Lancet 2000, 355, 911-918.
Ketter, T.A. et al., J. Clin. Psychiatry 1995, 56, 471-475.
Keung W.M. et al, "Daidzin and daidzein suppress free-choice ethanol intake by Syrian golden hamsters" Proc Natl Acad Sci, vol. 90, p. 1008-10012, Nov. 1993.
Kohno, H. et al.: "A Novel Synthesis of Isoquinolines Containing an Electron Withdrawing Substitute". Heterocycles, vol. 51, No. 1, 1999, pp. 103-117.
Kralinsky E.A. Tramal in the treatment of pain in children with malignancies XP002162259 English Abstract & Klinicka Onkologie, vol. 7, No. 6, 1994, pp. 182-185.
Kunkler et al., "Hippocampal Spreading Depression Bilaterally Activates the Caudal Trigeminal Nucleus in Roadent", Hippocampus 13:835-844 (2003).
Kuzniecky et al., "Topiramate increases cerebral GABA in healthy humans", Neurology (Aug. 1998) 51(2) pp. 627-629.
Kyowa Hakko, "Topiramate" Drugs of the Future, ES, Barcelona, vol. 21, No. 4, Jan. 1, 1996; p. 463-465, XP002043895.
Langtry H.D. et al, "Topiramate, A review of its pharmacodynamic and pharmacokinetic properties and clinical efficacy in the management of epilepsy" Drugs, (1997) 54/5 pp. 752-773, XP002179441.
Lydiard, R.B. et al., J. Clin. Psychiatry 1998, 59, Suppl. 18, 10-17.
Maryanoff, B.E. et al.: "Structure-Activity Studies on Anticonvulsant Sugar Sulphmates Related to Topiramate. Enhanced Potency with Cyclic Sulphate Derivatives". Journal of Medicinal Chemistry, vol. 41, No. 8, 1998, pp. 1315-1343, XP002149867.
Mathew, Ninan T., MD, et al, "Prophylaxis of Migraine, Transformed Migraine, and Cluster Headache with Topiramate" Headache (2002), (42)796-803.
Mathew, N. T. "Antiepileptic Drugs in Migraine Prevention", 2001, Headache, November/December Suppl 2001, pp. S18-S24.
Mazzotta et al., J Headache Pain, 2004 5:S67-S70.
McElroy, S.L. et al., "A pilot trial of adjunctive topiramate in the treatment of bipolar disorder ADIS Title: Topiramate: therapeutic use; Bipolar disorder: A pilot trial of adjunctive treatment" retrieved from STN Database Accession No. 1998:39968 XP00217779443 Abstract & XXIST CINP Congress (Jul. 12, 1998) pp. 281 (Poster) University of Cincinnati College of Medicine, Cincinnati, OH.
Mueller T I, "A double-blind, placebo-controlled pilot study of carbamazepine for the treatment of alcohol dependence", Alcoholism Clin Exp Res, vol. 21, No. 1, 1997, p. 86-92, X00913485.
Moller, H.J. et al., Eur. Arch. Psychiatry Clin. Neurosci. 2000, 250, 57-68.
Moskowitz, M.A., "The Neurobiology of Vascular Head Pain", Annals of Neurology, vol. 16, Issue 2, pp. 157-168, 1984.
Mula et al., "The role of anticonvulsant drugs in anxiety disorders: a critical review of the eVidence" Journal of Clinical Psychopharmacology, Williams and Wilkins, vo 1.27, No. 3, 2007, pp. 263-272.
Myers, R.D., "New Drugs for the Treatment of Experimental Alcoholism", Alcohol, vol. 11, No. 6, 1994, p. 439-451.
Nemeroff, C.B., Depress. Anxiety 1996-1997, 4, 169-181.
Nickel et al., Journal of Affective Disorders, vol. 87(2-3), 2005, pp. 243-252.
Nies et al., Goodman & Gilman's The Pharmacological Basis of Therapeutics, 9th Edition, pp. 43-62, 1996.
Olesen et al., "Spreading Cerebral Oligemia in Classical- and Normal Cerebral Blood Flow in Common Migraine", Department of Neuromedicine, Rigshospitalet 2100 Copenhagen, Denmark, Jan. 28, 1982 (Headache 22:242-248, 1982).
Olson et al [Editors]. Remington's Pharmaceutical Sciences, pp. 420-425, 1980.
Osborne et al, Abstract, Topiramate Improves Glycemic Control and Triglycerides in Animal Models 1 page The Posters were presented at the American Diabetes Association Conference held Jun. 22-26 in Philadelphia, diabetes, A Journal of the American Diabetes Association, Abstract Book 61st Scientific Sessions Friday, Jun. 22-Tuesday Jun. 26, 2001, 1255-P, A302.
Ottman et al., "Comorbidity of migraine and epilepsy", Neurology, 1994;44: 2105 (Abstract only).
Pansare, S.V. et al.: "Intramolecular Imine Cross-Coupling in Dibenzylidine Sulphamides; synthesis of unsymmetrical 1,2-diaryl ethanediamines". Tetrahedron Letters, vol. 37, No. 16, Apr. 15, 1996, pp. 2859-2862, XP004029817.
Pascual D et al: "A cannabinoid agonist, WIN55,212-2, reduces neuropathic nocicipetion induced by paclitaxel in rats" Pain 118:23-34, 2005.
Penovich et al., "Weight Loss in Patients Receiving Topiramate for Intractable Epilepsy", 1994, Neurology 44 (Suppl. 2) Abstract 309P, 46th Annual Meeting of the American Academy of Neurology, Washington, D.C.
Perry et al. "Sumatriptan: An Updated Review of its Use in Migraine", 1998, Drugs, vol. 55, No. 6, pp. 889-922.
Pini et al., "Anti-Epileptic Drugs in the Preventive Treatment of Migraine Headache: a Brief Review", (J. Headache Pain, 2001, 2:13-19.
Polomano et al: "A painful peripheral neuropathy in the rat produced by the chemotherapeutic drug, paclitaxel", Pain, 94:293-304, 2001.
Prado Lima, P.A.S. et al., "Topiramate in treatment-refractory depression" retrieved from STN Database accession No. 1999:61852 XP002179442 Abstract & 11$^{th}$ World Congress of Psychiatry (Aug. 6, 1999), vol. 2,00.126.
Raguraman, et al., "Effects of topiramate in alcohol dependence [2]" Australian and New Zealand Journal of Psychiatry, 2005 Australia, vol. 39, No. 8, 2005, pp. 736-737.
Ramlo-Halsted BA, "The Natural History of Type 2 Diabetes", Primary Care Dec. 1999;26(4):771-89.
Reis et al. Craving decrease with topiramate in outpatient treatment for cocaine dependence: an open label trial, Rev Bras Psiquiatr 2008;30(2):132-5.
Rogaswki et al., Nature Medicine, vol. 10, No. 7, Jul. 2004, pp. 685-692.
Rogawski et al., Nature Reviews Neuroscience, vol. 5 (1), 2004, pp. 553-564.
Rost et al., The effect of tramadol and other analgesics on the pain..., Abstract, Arzneim-Forsch. 1978, vol. 28 (1a0 pp ... 181-183).
Rouillon, F., Eur. Neuropsychopharmacol 1999, 9 Suppl. 3, S87-S92.
Sanacora, G. et al., "Impairment of GAB Aergic transmission in depression: New Insights from neuroimaging studies", Critical Reviews in Neurobiology, (2000) 14/1 pp. 23-45, XP001029967, whole document.
Sharma K, McCue P, Dunn SR. Am J Physiol Renal Physiol. Jun. 2003;284(6):F1138-44.
Silberstein et al., "Migraine & Epilepsy", www.myepilepsy.com, 2002.
Sofuoglu et al., CNS Drugs 2005: 19(1), pp. 13-25.
Soledade et al.: "Toward the control of *Leptosphaeria maculans*" Design, Synthesis, biological activity, and metabolism of potential detoxification inhibitors of the crucifer phytoalexin brassinin. Bioorganic & Medicinal Chemistry, vol. 14, No. 14, Apr. 17, 2006, pp. 4958-4979, XP005458688.
Stephen, Linda J. et al., "Lamotrigine and topiramate may be a useful combination", The Lancet, vol. 351, No. 9107, pp. 958-959, 1998.
Stephen, Linda J. et al., "Topiramate in Refractory Epilepsy: A Prospective Observational Study", Epilepsia, vol. 41, No. 8, pp. 977-980, 2000.
Storey et al, "Topiramate in Migraine Prevention: A Double Blind, Placebo-Controlled Study", 2001, Headache, 41, pp. 968-975.
Ten Have, R. et al.: "Novel Synthesis of 4(5)-monosubstituted imidazoles via cycloaddition of tosylmethyl isocyanide to aldimines". Tetrahedron, vol. 53, No. 33, Aug. 18, 1997, pp. 11355-11368, XP004106007.
The Merck Manual, 1999, Merck Research, Whitehouse Station, NJ XP002224345, Diabetes Mellitus, pp. 165-177.
The Merck Manual (1987), Merck Sharp & Dohme Research Laboratories, Rahway, NJ XP002144176, pp. 1351-1356.
Topiramate retrieved from STN Database Accession No. 1998:2562 XP002179444 Abstract & R&D Focus Drug News, Jul. 27, 1998.

(56) References Cited

OTHER PUBLICATIONS

Traube, W. et al.: "Zur Kenntnis des Sulfamids". Berichte der Deutschen Chemischen Gesellschaft, vol. 56, 1923, pp. 1656-1663, XP002393747.
Uys et al., CNS Neurol Disord Drug Targets, 7(5), 2008, pp. 482-91.
Van Amerigen et al. Antiepileptic drugs in the treatment of anxiety disorders: Role in Therapy, Drugs, 2004, 64(19), 2199-2220.
Vandi, A., et al.: "Synthesis and Properties of Some N-Substituted Sulphamides", Journal of Organic Chemistry, vol. 26, No. 4, Apr. 1961, pp. 1136-1138, XP002394144.
Von Seggern, Randal L., et al, "Efficacy of Topiramate in Migraine Prophylaxis: A Retrospective Chart Analysis" Headache (2002), (42)804-809.
Wauquier A et al, "Topiramate: A potent anticonvulsant I the Amygdala-Kindled Rat" Epilepsy Research, NJ, Elsevier Science Publishers, Amsterdam, vol. 24, No. 2, Jun. 1, 1996, p. 73-77, XP002042953.
WebMD Medical News Epilepsy Drugs Fights Migraine, 2002, www.webmd.com/migraine-headaches/news/20020923/epilepsydrug-fights-migraine.
Weib, G. et al.: "Herstellung and Reaktionen von N-Monoalkylamidosulfonylchloriden" Liebigs Annalen Der Chemie, vol. 729, Dec. 1969, pp. 40-51, XP002187581 (English Abstract provided).
Wheeler et al., "Topiramate-treated cluster headache", Neurology (Jul 1999) vol. 53, No. 1 pp. 234-236.
Wheeler S.D., "Antiepileptic Drug therapy in Migraine Headache", Current Treatment Options Neurology, Sep. 2002; 4(5):383-394.
Wheeler, "Significance of migrainouse features in cluster headache", Headache (1998) 38/7 pp. 547-551.
Whitehead, C.W. et al.: "Diuretics. II. Alkoxymercuration oby mixed anion sales of mercury". Journal of the American Chemical Society, vol. 80, No. 9, May 5, 1958, pp. 2182-2185, XP002393746.
Williams, Jr., J.W., et al., Ann. Intern. Med. 2000, 132, 743-756.
York, DA et al, "Effects of Topirament on High Fat Diet-Induced Obesity", FASEB journal, Fed. Of America Soc. For Experimental Biology, Bethesda, MD, US., vol. 14, No. 4, Apr. 2000. p. A431, XP000915192.
Young, WB et al, "Topiramate: a case series study in migraine prophylaxis" Cephalalgia (2002), (22)659-663.
Ziegler. E., et al.: "Zur Reaktivitat von C=Ndoppelbindungssytemen, VI. Reaktionen mit Sulfonamiden und Sulfamiden". Zeitschrift Fur Naturforschung, vol. 30B, 1975, pp. 951-953, XP008067475.
Chemische Berichte, 1959, 92, pp. 509-513 (see English translation provided).
Alcaraz et al., Org. Lett., 2004, 6(16), pp. 2705-2708.
Beaudoin et al., J. Org. Chem., 2003, 68, pp. 115-119.
Birch et al., J. Med. Chem., 1999, 42, pp. 3342-3355.
Delgado et al., Tet Lett, 1988, 29(3), pp. 3671-3676.
Estave et al., Tet Lett, 2002, 43, pp. 1019-1021.
Gavernet et al., Bioorg & Med Chem., 2007, 15, pp. 5604-4516.
Hedayatullah et al., Phosphorus and Sulfur, 1985, 25(1), pp. 33-38.
Hirayama et al., Bioorg & Med Chem., 2002, 10, pp. 1509-1523.
Kubicki et al., J Mol Struct., 2001, 531(1-3), p. 65-70.
Lee et al., Org. Chem 1990 55(25) pp. 6098-6104.
Muniz et al., SYNLETT, 2005, 1, pp. 149-151.
Nelson et al., J. Med. Chem., 1977, 20(7), pp. 880-885.
Nelson et al., J. Med. Chem., 1979, 22(9), pp. 1125-1127.
Nicolaou et al., Chem. Eur. J., 2004, 10, pp. 5581-5606.
Okada et al., Tet Lett, 2000, 41, pp. 7047-7051.
Park et al., J. Med. Chem., 2002, 45, pp. 5295-5302.
Winum et al., Org. Lett., 2001, 3(14), pp. 2241-2243.
Xu et al., SYNLETT, 2004, 11, pp. 1901-1904.
Zhong et al., J. Comb. Chem., 2004, 6, pp. 556-563.
Agrawal et al., Bioorganic and Medicinal Chemistry, 11(2003), pp. 5353-5362.
Casini et al., Bioorganic and Medicinal Chemistry Letters, 13(2003), pp. 841-845.
Pasorekova et al., Journal of Enzyme Inhibition and Medicinal Chemistry, Jun. 2004, vol. 19(3), pp. 199-229.
Supuran et al., Curr. Med. Chem.—Cardiovascular and Hematological Agents, 2004, 2, pp. 49-68.
Supuran et al., Curr. Med. Chem.—Imm., Endoc. & Metab Agents, 2001, 1, 61-97.
Supuran et al., Exp. Opin. Ther. Patents, (2000), 10(5), pp. 575-600.
Supuran et al., Medicinal Research Reviews, vol. 23, No. 2, pp. 146-189, 2003.
Thakur at al., Bioorganic and Medicinal Chemistry, 12(2004), pp. 789-793.
Desagher et al., The Journal of Neuroscience, 1996, 16(8), pp. 2553-2562.
Tabner et al., The Journal of Biological Chemistry, vol. 280, No. 43, pp. 35789-35792, Oct. 28, 2005.
Taylor et al., Science, vol. 296, pp. 1991-1995 (2002).
Office Action mailed Mar. 26, 2008 in U.S. Appl. No. 11/154,443.
Notice of Allowance mailed Dec. 31, 2008 in U.S. Appl. No. 11/154,443.
Notice of Allowance mailed Jun. 8, 2009 in U.S. Appl. No. 11/154,443.
Notice of Allowance mailed Oct. 9, 2009 in U.S. Appl. No. 11/154,443.
Notice of Allowance dated Feb. 9, 2010 in U.S. Appl. No. 11/154,443.
Notice of Allowance dated May 25, 2010 in U.S. Appl. No. 11/154,443.
Office Action mailed Oct. 3, 2007 in U.S. Appl. No. 11/154,386.
Office Action mailed Jul. 9, 2008 in U.S. Appl. No. 11/154,386.
Notice of Allowance mailed Mar. 6, 2009 in U.S. Appl. No. 11/154,386.
Notice of Allowance mailed Sep. 10, 2009 in U.S. Appl. No. 11/154,386.
Notice of Allowance dated Feb. 23, 2010 in U.S. Appl. No. 11/154,386.
Office Action mailed Apr. 14, 2008 in U.S. Appl. No. 11/209,122.
Notice of Allowance mailed Oct. 30, 2008 in U.S. Appl. No. 11/209,122.
Office Action mailed Mar. 20, 2009 in U.S. Appl. No. 11/209,122.
Notice of Allowance mailed Sep. 24, 2009 in U.S. Appl. No. 11/209,122.
Notice of Allowance mailed Jan. 13, 2010 in U.S. Appl. No. 11/209,122.
Office Action mailed Sep. 10, 2008 in U.S. Appl. No. 11/406,794.
Notice of Allowance dated Mar. 13, 2009 in U.S. Appl. No. 11/406,794.
Notice of Allowance dated Jul. 17, 2009 in U.S. Appl. No. 11/406,794.
Office Action mailed Nov. 2, 2009 in U.S. Appl. No. 11/406,794.
Notice of Allowance dated Mar. 17, 2010 in U.S. Appl. No. 11/406,794.
Notice of Allowance dated Jul. 1, 2010 in U.S. Appl. No. 11/406,794.
Office Action mailed Aug. 17, 2009 in U.S. Appl. No. 11/611,938.
Final Office Action mailed Feb. 25, 2010 in U.S. Appl. No. 11/611,938.
Office Action mailed May 2, 2008 in U.S. Appl. No. 11/611,961.
Final Office Action mailed Jan. 28, 2009 in U.S. Appl. No. 11/611,961.
Notice of Allowance mailed Jun. 2, 2009 in U.S. Appl. No. 11/611,961.
Notice of Allowance mailed Jan. 6, 2010 in U.S. Appl. No. 11/611,961.
Notice of Allowance mailed Apr. 30, 2010 in U.S. Appl. No. 11/611,961.
Office Action mailed Nov. 26, 2008 in U.S. Appl. No. 11/612,071.
Final Office Action mailed Jun. 8, 2009 in U.S. Appl. No. 11/612,071.
Office Action mailed Aug. 5, 2008 in U.S. Appl. No. 11/612,146.
Final Office Action mailed Oct. 29, 2009 in U.S. Appl. No. 11/612,146.
Office Action mailed Jan. 29, 2009 in U.S. Appl. No. 11/612,174.
Office Action mailed Mar. 30, 2009 in U.S. Appl. No. 11/612,202.
Office Action mailed Jan. 14, 2010 in U.S. Appl. No. 11/612,202.
Notice of Allowance mailed Jul. 29, 2010 in U.S. Appl. No. 11/612,202.
Office Action dated Jul. 9, 2010 in U.S. Appl. No. 11/612,222.

(56) References Cited

OTHER PUBLICATIONS

Office Action mailed Jul. 21, 2009 in U.S. Appl. No. 11/612,249.
Final Office Action mailed Jan. 28, 2010 in U.S. Appl. No. 11/612,249.
Office Action mailed May 21, 2008 in U.S. Appl. No. 11/674,021.
Final Office Action mailed Jul. 31, 2009 in U.S. Appl. No. 11/674,021.
Notice of Allowance mailed Jun. 16, 2010 in U.S. Appl. No. 11/674,021.
Office Action mailed Jun. 24, 2009 in U.S. Appl. No. 12/055,433.
Final Office Action mailed Feb. 23, 2010 in U.S. Appl. No. 12/055,433.
Office Action dated Jun. 1, 2010 in U.S. Appl. No. 12/488,079.
Maryanoff et al.: Anticonvulsant O-Alkyl Sulfamates 2,3:4,5-Bis-O-(1-methylethylidene)-betas-D-fructopyranose Sulfamate and Related Compounds, J.Med. Chem., vol. 30, No. 5, 1987, pp. 880-887.
Maryanoff et al.: "Comparison of Sulfamates and Sulfamide Groups for the Inhibition of Carbonci Anhydrase-II by Using Topiratmate as a Structural Platform", J. Med. Chem, vol. 48, No. 6, 2004, pp. 1941-1947.
Levy RH et al., eds. Antiepileptic Drugs. 3$^{rd}$ ed. New York: Raven Press, 1989:85-102.
CA PLUS 835894-67-2 Sulfamic acid (1,3-benzodioxo1-2-ylmethyl ester), (Feb. 23, 2005).
CA PLUS 835894-65-0 Sulfamide [(3, 4-dihydro-2H-1-benzopyran-2-yl) methyl], (Feb. 23, 2005).
CA PLUS 835894-63-8 Sulfamic acid (3,4-dihydro-2H-1-benzopyran-2-yl)methyl ester, (Feb. 23, 2005).
Malatynska et al., "Submissive behavior in mice as a test for antidepressant drug activity", Neuroscience and Biobehavioral Review, 82 (2005) 306-313.
Malatynska et al., "Dominant-submissive behavior as models of mania and depression", Neuroscience and Biobehavioral Review, 29 (2005) 715-737.
Ghaemi et al., Soc. of Bio. Psychiatry, (1999) vol. 45, 137-144.
Stoll et al., Harvard Rev. Psychiatry, July/August 1996, vol. 4, No. 2, 77-89.
Rygula et al., "Anhedonia and motivational deficits in rats: Impact of chronic encini stress", Behavioral Brain Resenrch, 160 (0005) 127-134.
Scozzafava A et al, "Modulaton of Carbonic Anhydrase Activity and Its Applications in Therapy", Expert Opinion on Therapeutic Patents 2003 United Kingdom, vol. 14, No. 5 (2004) pp. 667-702, XP002331413, ISSN:1354-3776.
Harrison'S Principles of Internal Medicine, vol. 2, 23d ed., Ed by Isselbacher, Braunwald, Wilson, Martin, Fauci and Kasper, McGraw-Hill Inc New York City, 1994, p. 2275.
Angehagen, Mikael et al., "Does topiramate (TPM) have protective effects on astroglia cells and neurons in primary cortical cultures", Epilepsia, (1998) vol. 39, No. Suppl 6, pp. 44, XP000923162 abstract 2.050.
Meldrum B. et al., "Excitatory amino acid neurotoxicity and neurodegenerative disease" TIPS, vol. 11, 1990, pp. 379-387, XP000915223.
Yang Y. et al., "Neuroprotection by delayed administration of topiratmate in rat model of middle cerebral artery embolization", Brain Research, vol. 804, No. 2, 1998, pp. 169-176, XP000921218.
Notice of Allowance dated Sep. 20, 2010 in U.S. Appl. No. 11/154,443.
Notice of Allowance dated Jan. 25, 2011 in U.S. Appl. No. 11/154,443.
Notice of Allowance dated Oct. 22, 2010 in U.S. Appl. No. 11/154,386.
Notice of Allowance dated Jan. 11, 2011 in U.S. Appl. No. 11/209,122.
Notice of Allowance dated Nov. 29, 2010 in U.S. Appl. No. 11/406,794.
Notice of Allowance dated Aug. 12, 2010 in U.S. Appl. No. 11/611,961.
Notice of Allowance dated Nov. 30, 2010 in U.S. Appl. No. 11/611,961.
Office Action mailed Nov. 15, 2010 in U.S. Appl. No. 11/612,202.
Notice of Allowance mailed Mar. 4, 2011 in U.S. Appl. No. 11/612,202.
Office Action mailed Oct. 15, 2010 in U.S. Appl. No. 11/612,249.
Notice of Allowance mailed Dec. 15, 2010 in U.S. Appl. No. 11/674,021.
Office Action mailed Sep. 22, 2010 in U.S. Appl. No. 12/055,433.
Office Action mailed Nov. 15, 2010 in U.S. Appl. No. 12/055,924.
Notice of Allowance mailed Dec. 14, 2010 in U.S. Appl. No. 12/488,079.
Handley and Mithani, Naunyn. Schmied. Arch. Pharmacol., 327, 1-5, 1984.
Aron et al., Neuropharmacology, 10, 459-469, 1971.
Meert et al., *Pharmacol. Biochem. Behav.*; 2005, 80(2), pp. 309-326.
MacDonald et al., CNS Drugs, 2002, 16(8): 549-562.
Walden et al., Neuropsychobiology, 1998,38: 181-84.
Byrn et al., Pharmaceutical Research, Kluwer Academic Publishers, New York, NY, US, vol. 12, No. 7, 1995, pp. 945-954.
Johns Hopkins Clinical Trial of Topiramate for Cocaine Addiction (ClinicalTrials.gov), 2009.
Keck, P. et al, "Valproate and carbamazepine in the treatment of panic and post traumatic stress disorders, withdrawals states . . . " J Clin Psychopharm, vol. 12, No. 1, p.36S-41S, 1992.
Migraine: Treatments and drugs, by Mayo Clinic Staff, http://www.mayoclinic.com/health/migraineheadache/DS00120/DSECTION=treatments-and-drugs, Jun. 6, 2009.
Uhart et al., Addiction Biology, 14, pp. 43-64, 2008.
Winhusen et al. Drug and Alcohol Dependence 91 (207) 131-148, 2007.
Kim et al., Tet Lett 23(14) pp. 1505-1508 (2000).
Supuran et al., Exp. Opin. Ther. Patents, (2002), 12(2), pp. 217-242.
Behl et al., Endocrinology, vol. 138, No. 1, pp. 101-106, 1997.
Coyle et al., Science, vol. 262, Issue 5134, pp. 689-695, 1993.
Bernando, L., Prevention of epilepsy after head trauma: do we need drugs or a new approach?, 2003, Epilepsia, 44, (Suppl. 10), 27-33.
D'Ambrosio et al., Curr. Opin. Neurol. Dec. 2004; 17(6): 731-735.
Jones et al. "Screening for Major Depression in Epilepsy with Common Self-Report Depression Inventories", Epilepsia, May 2005; 46(5):731-735.
Kane et al., Psychopharmacological Bulletin, vol. 24, pp. 62-67 (1988).
Kaplan & Sadock's Comprehensive Textbook of Psychiatry, Seventh Edition, vol. II, Lippincott Williams & Wilkins: Philadelphia, pp. 2467-2468, 2000.
Kaplan & Sadock's Comprehensive Textbook of Psychiatry, Seventh Edition, vol. II, Lippincott Williams & Wilkins: Philadelphia, pp. 2470-2471, 2000.
Physician's Desk Reference; Kaplan & Sadock's Comprehensive Textbook of Psychiatry, Seventh Edition, vol. II, Lippincott Williams & Wilkins: Philadelphia, pp. 2466-2467, 2000 (olanzapine).
Physician's Desk Reference; Kaplan & Sadock's Comprehensive Textbook of Psychiatry, Seventh Edition, vol. II, Lippincott Williams & Wilkins: Philadelphia, pp. 2456-2463, 2000 (clozapine).
Physician's Desk Reference; Kaplan & Sadock's Comprehensive Textbook of Psychiatry, Seventh Edition, vol. II, Lippincott Williams & Wilkins: Philadelphia, pp. 2463-2466, 2000 (risperidone).
Physician's Desk Reference; Kaplan & Sadock's Comprehensive Textbook of Psychiatry, Seventh Edition, vol. II, Lippincott Williams & Wilkins: Philadelphia, pp. 2469-2470, 2000 (quetiapine).
Ca 835894-69-4 Sulfamide (1,3-benzodioxol-2-ylmethyl) (2005).
Harwood, AJ, Molecular Psychiatry (2005) 10,117-126.
Sullivan, P., Epilepsy & Behavior 7 (2005) S12-S17.
Notice of Allowance dated Mar. 20, 2012 in U.S. Appl. No. 11/209,122.
Notice of Allowance dated Jan. 17, 2012 in U.S. Appl. No. 11/406,794.
Notice of Allowance dated Feb. 6, 2012 in U.S. Appl. No. 11/611,961.
Notice of Allowance mailed Mar. 9, 2012 in U.S. Appl. No. 11/612,071.

(56) References Cited

OTHER PUBLICATIONS

Final Office Action mailed Dec. 15, 2011 in U.S. Appl. No. 12/431,141.
Notice of Allowance mailed Jan. 4, 2012 in U.S. Appl. No. 11/612,202.
Office Action mailed Dec. 22, 2011 in U.S. Appl. No. 12/055,433.
Final Office Action mailed Nov. 21, 2011 in U.S. Appl. No. 12/055,695.
Notice of Allowance mailed Nov. 1, 2011 in U.S. Appl. No. 12/488,079.
Notice of Allowance dated Mar. 1, 2012 in U.S. Appl. No. 12/488,079.
Notice of Allowance mailed Nov. 28, 2011 in U.S. Appl. No. 12/502,472.
Brandt et al., Neuropsychobiology, 1998, 38, pp. 202 to 203.
Brodie, M.S.; Pesold, C; Appel, S.B. Alcohol Clin Exp Res 1999, 23, pp. 1848-1852.
Dib, Jean G., Current Medical Research and Opinion, 2004, 20, 12, p. 1857-1861.
Edeh et al, (1987) Relationship between interictal psychopathology and the type of epilepsy. Results of a survey in general practice. Br J Psychiatry 151:95-101.
Ettinger et al., (2004) Depression and comorbidity in community-based patients with epilepsy or asthma. Neurology 63:1008-1014.
Forsgren et al., (1990) An incident case-referent study of epileptic seizures in adults. Epilepsy Res 6:66-81.
Hesdorffer et al. (2006) Depression and suicide attempt as risk factors for incident unprovoked seizures. Ann Neurol 59:35-41.
Hesdorffer et al. (2000) Major depression is a risk factor for seizures in older adults. Ann Neurol 47:246-249.
Jacoby et al. (1996) The clinical course of epilepsy and its psychosocial correlates: findings from a U.K. Community study. Epilepsia 37:148-161.
Kanner, AM., (2006) Epilepsy, suicidal behaviour, and depression: do they share common pathogenic mechanisms? Lancet Neurol 5:107-108.
Keck et al., J. Clin. Psychiatry, 2002, 63 (suppl 4).
Krampfl et al., The European Journal of Neuroscience; vol. 22, Issue: 1, pp. 10-20, 2005.
Ottman et al., Epilepsia, 52(2):308-315, 2011.
Scimemi et al., The Journal of Neuroscience: the official journal of Society for Neuroscience; vol. 25; Issue: 43, pp. 10016-10024, 2005.
Tanimukai et al., International Pharmacopsychiatry, 1970, vol. 5, No. 1, pp. 35 to 43.
Thienel et al., Acta Neurologica Scandinavica, 2004, 110, 4, p. 221-231.
Wise RA, Drug Alcohol Depend, 1998, 51, pp. 13-22.
Wise RA, NIDA Res Mono, 1984, 50, pp. 15-33.
Notice of Allowance dated Jul. 19, 2012 in U.S. Appl. No. 11/154,386.
Notice of Allowance dated Nov. 20, 2012 in U.S. Appl. No. 11/154,386.
Notice of Allowance dated May 10, 2012 in U.S. Appl. No. 11/406,794.
Notice of Allowance dated May 23, 2012 in U.S. Appl. No. 11/611,961.
Notice of Allowance dated Aug. 27, 2012 in U.S. Appl. No. 11/611,961.
Notice of Allowance mailed Apr. 25, 2012 in U.S. Appl. No. 11/612,146.
Interview Summary mailed Mar. 26, 2012 in U.S. Appl. No. 12/431,141.
Notice of Allowance mailed Apr. 16, 2012 in U.S. Appl. No. 11/612,202.
Notice of Allowance mailed Aug. 9, 2012 in U.S. Appl. No. 11/612,202.
Notice of Allowance mailed Nov. 26, 2012 in U.S. Appl. No. 11/612,202.
Notice of Allowance dated May 11, 2012 in U.S. Appl. No. 13/301,109.
Interview Summary mailed Apr. 4, 2012 in U.S. Appl. No. 12/055,433.
Notice of Allowance dated May 11, 2012 in U.S. Appl. No. 12/349,184.
Notice of Allowance mailed Jun. 18, 2012 in U.S. Appl. No. 12/488,079.
Notice of Allowance mailed Oct. 10, 2012 in U.S. Appl. No. 12/488,079.
Notice of Allowance mailed Mar. 28, 2012 in U.S. Appl. No. 12/502,472.
Notice of Allowance mailed Jul. 16, 2012 in U.S. Appl. No. 12/502,472.
Notice of Allowance dated May 10, 2013 in U.S. Appl. No. 11/209,122.
Notice of Allowance mailed Dec. 24, 2012 in U.S. Appl. No. 11/611,938.
Notice of Allowance mailed Mar. 27, 2013 in U.S. Appl. No. 11/611,938.
Notice of Allowance dated Dec. 10, 2012 in U.S. Appl. No. 11/611,961.
Notice of Allowance dated Apr. 2, 2013 in U.S. Appl. No. 11/611,961.
Notice of Allowance mailed Jan. 22, 2013 in U.S. Appl. No. 11/612,071.
Notice of Allowance mailed Mar. 18, 2013 in U.S. Appl. No. 11/612,202.
Office Action mailed May 23, 2013 in U.S. Appl. No. 12/055,433.
Notice of Allowance mailed Feb. 7, 2013 in U.S. Appl. No. 12/488,079.
Notice of Allowance mailed Mar. 27, 2013 in U.S. Appl. No. 12/488,079.
Notice of Allowance mailed Apr. 29, 2013 in U.S. Appl. No. 12/502,472.
Remington's The Science and Practice of Pharmacy, 19th Edition, Published 1998, vol. I, pp. 371-375.
Remington's The Science and Practice of Pharmacy, 19th Edition, Published 1998, vol. II, pp. 2226-2241 [See attached translation as provided from foreign agent in Colombia, detailing only portions of the article as cited by the Colombian examiner containing indications regarding the general procedures for manufacturing, isolating and purifying crystals and polymorphs].
Stella et al., Drugs, 29: 455-473 (1985).
Benjamin et al. J Biomol Screening, 2006, vol. 11, pp. 29-39.
Brown et al. Tetrahedron, 1987, vol. 43, pp. 4071-4078.
Dunham et al. J Am Pharm Assoc Sci Ed, 1957, vol. 46, pp. 208-209.
Ettinger et al. Neurotherapeutics, 2007, vol. 4, pp. 75-83.
Gavernet et al. Bioorg Med Chem 2007, vol. 15, pp. 1556-1567.
Gavernet et al. J Med Chem, 2009, vol. 52, pp. 1592-1601.
Gribkoff, V., Expert Opin Ther Pat., 2003 vol. 7, pp. 737-748.
Kohling, R., Epilepsia, 2002, vol. 43, pp. 1278-1295.
Kuzimski et al., Epilepsia, 2005, vol. 46, pp. 481-489.
Landmark, C., CNS Drugs, 2008, vol. 22, pp. 27-47.
Liu et al., Epilepsy Res, 2006, vol. 70, pp. 263-268.
Liu et al., Neuropharmacology, 2003, vol. 44, pp. 413-422.
Lombardo et al., Mol Brain Res, 1996, vol. 35, pp. 84-90.
Lothman et al., Epilepsy Res, 1988, vol. 2, pp. 356-366.
Lothman et al., Epilepsy Res, 1988, vol. 2, pp. 367-379.
Lukyanetz et al., Epilepsia, 2002, vol. 43, pp. 9-18.
Maryanoff et al, Drugs Future, 1989, vol. 14, pp. 342-344.
Maryanoff et al, J Med Chem, 2008, vol. 51, pp. 2518-2521.
Maryanoff et al., Curr Top Med Chem, 2009, vol. 9, pp. 1049-1062.
Maryanoff, B., J Med Chem, 2009, vol. 52, pp. 3431-3440.
Orloff et al., Proc Soc Exp Biol Med, 1949, vol. 70, pp. 254-257.
Parker et al., J Med Chem, 2009, vol. 52, pp. 7528-7536.
Rogawski et al., Nat Med, 2004, vol. 10, pp. 685-692.
Rogawski, M., Epilepsy Res, 2006, vol. 69, pp. 273-294.
Shank et al., CNS Neurosci Ther, 2008, vol. 14, pp. 120-142.
Shank et al., Epilepsia, 1994, vol. 35, pp. 450-460.
Shank et al., J Enzym Inh Med Chem, 2008, vol. 23, pp. 271-276.
Shingles et al., Anal Biochem, 1997, vol. 252, pp. 190-197.
Soderpalm, B., Eur J Pain, 2002, vol. 6, Suppl A, pp. 3-9.
Swinyard et al., J Pharmacol Exp Ther, 1952, vol. 106, pp. 319-330.
Swinyard, E., Epilepsia, 1969, vol. 10, pp. 107-119.
Wang et al., Science, 1998 vol. 282, pp. 1890-1893.

(56) References Cited

OTHER PUBLICATIONS

White et al., Antiepileptic Drugs, 5th Ed., 2002, pp. 36-48.
White et al., Epilepsy Res, 1992, vol. 12, pp. 217-226.
White et al., Int Rev Neurobiol, 2007, vol. 81, pp. 85-110.
Winum et al., Expert Opin Ther Pat, 2006, vol. 16, pp. 27-47.
Zaremba et al., Pharmacol Rep, 2006, vol. 58, pp. 1-12.
Loscher, et al., Pharma. Rev., 62, 668-700 (2010).
Walker, et al., Brain, 125, 1937-1950 (2002).
Loscher et al. Antiepileptogenic effects of the novel anticonvulsant levetiracetam (ucb L059) in the kindling model of temporal lobe epilepsy. The Journal of Pharmacology and Experimental Therapeutics, vol. 284, No. 2, 1998, pp. 474-479.
McNamara et al. Analyses of the molecular basis of kindling development. Psychiatry and Clinical Neurosciences, 1995, 49, S175-S178.
Amano K, Hamada K, Yagi K, Seino M. Antiepileptic effects of topiramate on amygdaloid kindling in rats. Epilepsy Res. Jul. 1998;31(2):123-8.
Barton ME, White HS. The effect of CGX-1007 and CI-1041, novel NMDA receptor antagonists, on kindling acquisition and expression. Epilepsy Res. Mar. 2004;59(1):1-12.
Morimoto K, Katayama K, Inoue K, Sato K. Effects of competitive and noncompetitive NMDA receptor antagonists on kindling and LTP. Pharmacol Biochem Behav. Dec. 1991;40(4):893-9.
Racine, R.J. 1972. Modification of seizure activity by electrical stimulation. II. Motor seizure. Electroencephalogr. Clin. Neurophysiol. 32, 281-294.
Kinrys, G et al. Levetiracetam as Adjunctive Therapy for Refractory Anxiety Disorders. J. Clin. Psychiatry 68; Jul. 7, 2007: 1010-1013.
Kinrys, G et al. Levetiracetam or Treatment-Refractory Post-traumatic Stress Disorder J. Clin. Psychiatry 67:Feb. 2, 2006:211-214.
Zhang, W et al. Levetiracetam in social phobia: a placebo controlled pilot study. J. Psychopharm. 19(5) (2005) 551-553.
Nowack et al., Am J Physiol Cell Physiol, 299: C960-C967, 2010.
Notice of Allowance dated May 8, 2013 in U.S. Appl. No. 11/154,386.
Notice of Allowance dated Aug. 29, 2013 in U.S. Appl. No. 11/154,386.
Notice of Allowance dated Sep. 16, 2013 in U.S. Appl. No. 11/209,122.
Notice of Allowance dated Jul. 8, 2013 in U.S. Appl. No. 11/612,071.
Notice of Allowance mailed Sep. 23, 2013 in U.S. Appl. No. 11/612,146.
Office Action mailed Jul. 19, 2013 in U.S. Appl. No. 12/431,141.
Notice of Allowance mailed Jul. 9, 2013 in U.S. Appl. No. 11/612,202.
Notice of Allowance mailed Oct. 25, 2013 in U.S. Appl. No. 11/612,202.
Office Action mailed Aug. 6, 2013 in U.S. Appl. No. 11/612,222.
Notice of Allowance mailed Oct. 16, 2013 in U.S. Appl. No. 13/301,109.
Notice of Allowance mailed Aug. 9, 2013 in U.S. Appl. No. 12/488,079.
Notice of Allowance mailed Nov. 8, 2013 in U.S. Appl. No. 12/488,079.
Notice of Allowance dated Dec. 16, 2013 in U.S. Appl. No. 11/154,386.
Notice of Allowance dated May 7, 2014 in U.S. Appl. No. 11/154,386.
Notice of Allowance dated Feb. 20, 2014 in U.S. Appl. No. 11/209,122.
Notice of Allowance mailed Dec. 20, 2013 in U.S. Appl. No. 11/612,071.
Notice of Allowance mailed Mar. 31, 2014 in U.S. Appl. No. 11/612,146.
Final Office Action mailed Dec. 30, 2013 in U.S. Appl. No. 12/431,141.
Final Office Action mailed Jan. 16, 2014 in U.S. Appl. No. 11/612,222.
Notice of Allowance mailed May 21, 2014 in U.S. Appl. No. 11/612,222.
Final Office Action mailed Feb. 4, 2014 in U.S. Appl. No. 11/612,249.
Notice of Allowance dated Mar. 18, 2014 in U.S. Appl. No. 13/301,109.
Final Office Action mailed Nov. 14, 2013 in U.S. Appl. No. 12/055/433.
Notice of Allowance mailed Dec. 23, 2013 in U.S. Appl. No. 12/502,472.
Notice of Allowance mailed Apr. 24, 2014 in U.S. Appl. No. 12/502,472.
Otagiri et al., PRODRUG in "The New Drug Delivery System" (2000), CMC Publishing Co., Ltd., pp. 123-135 [translation of extracted portions from p. 124-subsection "2.2 Design of Prodrugs" and Table 1].
Mula et al. ("Psycopharmacology of topiramate: from epilepsy to bipolar disorder" in Neuropsychiatric Disease and Treatment 2006:2(4) 475-488).
Chengappa et al., "Topiramate as add-on treatment for patients with bipolar mania" in Bipolar Disorders, vol. 1, Issue 1, 42-53, Sep. 1999), Abstract attached.
Polymorphism in pharmaceutical solids, 1999, edited by H.G. Brittain, Mercel Decker; Grant (chapter 1), p. 1-10 and Guillory (chapter 5), p. 183-226.
Caria, Topics in Current Chemistry 1998, 198, 163-208.

* cited by examiner

CO-THERAPY FOR THE TREATMENT OF EPILEPSY AND RELATED DISORDERS

CROSS REFERENCE TO RELATED APPLICATIONS

This application claims the benefit of U.S. Provisional Application 60/802,000, filed on May 19, 2006, which is incorporated by reference herein in its entirety.

FIELD OF THE INVENTION

The present invention is directed to co-therapy for the treatment of epilepsy and related disorders comprising administering to a subject in need thereof, co-therapy with a therapeutically effective amount of a benzo-fused heterocycle sulfamide derivative and a therapeutically effective amount of one or more anticonvulsant and/or anti-epileptic agents.

BACKGROUND OF THE INVENTION

Epilepsy describes a condition in which a person has recurrent seizures due to a chronic, underlying process. Epilepsy refers to a clinical phenomenon rather than a single disease entity, since there are many forms and causes of epilepsy. Using a definition of epilepsy as two or more unprovoked seizures, the incidence of epilepsy is estimated at approximately 0.3 to 0.5 percent in different populations throughout the world, with the prevalence of epilepsy estimated at 5 to 10 people per 1000.

An essential step in the evaluation and management of a patient with a seizure is to determine the type of seizure that has occurred. The main characteristic that distinguishes the different categories of seizures is whether the seizure activity is partial (synonymous with focal) or generalized.

Partial seizures are those in which the seizure activity is restricted to discrete areas of the cerebral cortex. If consciousness is fully preserved during the seizure, the clinical manifestations are considered relatively simple and the seizure is termed a simple-partial seizure. If consciousness is impaired, the seizure is termed a complex-partial seizure. An important additional subgroup comprises those seizures that begin as partial seizures and then spread diffusely throughout the cortex, which are known as partial seizures with secondary generalization.

Generalized seizures involve diffuse regions of the brain simultaneously in a bilaterally symmetric fashion. Absence or petit mal seizures are characterized by sudden, brief lapses of consciousness without loss of postural control. Atypical absence seizures typically include a longer duration in the lapse of consciousness, less abrupt onset and cessation, and more obvious motor signs that may include focal or lateralizing features. Generalized Tonic-clonic or grand mal seizures, the main type of generalized seizures, are characterized by abrupt onset, without warning. The initial phase of the seizure is usually tonic contraction of muscles, impaired respiration, a marked enhancement of sympathetic tone leading to increased heart rate, blood pressure, and pupillary size. After 10-20 s, the tonic phase of the seizure typically evolves into the clonic phase, produced by the superimposition of periods of muscle relaxation on the tonic muscle contraction. The periods of relaxation progressively increase until the end of the ictal phase, which usually lasts no more than 1 min. The postictal phase is characterized by unresponsiveness, muscular flaccidity, and excessive salivation that can cause stridorous breathing and partial airway obstruction. Atonic seizures are characterized by sudden loss of postural muscle tone lasting 1-2 s. Consciousness is briefly impaired, but there is usually no postictal confusion. Myoclonic seizures are characterized by a sudden and brief muscle contraction that may involve one part of the body or the entire body.

There remains a need to provide an effective treatment for epilepsy and related disorders.

SUMMARY OF THE INVENTION

The present invention is directed to a method for the treatment of epilepsy and related disorders comprising administering to a subject in need thereof, co-therapy with a therapeutically effective amount of one or more anticonvulsant or anti-epileptic agents and a therapeutically effective amount of a compound of formula (I)

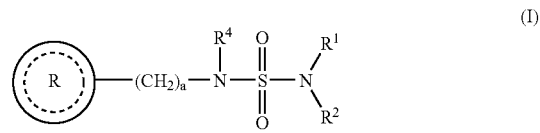

wherein $R^1$ and $R^2$ are each independently selected from the group consisting of hydrogen and lower alkyl;

$R^4$ is selected from the group consisting of hydrogen and lower alkyl;

a is an integer from 1 to 2;

is selected from the group consisting of

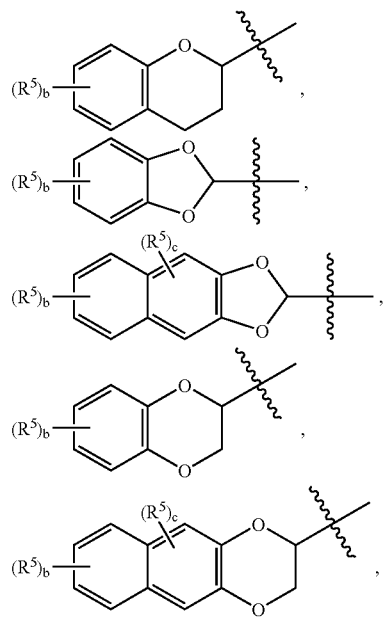

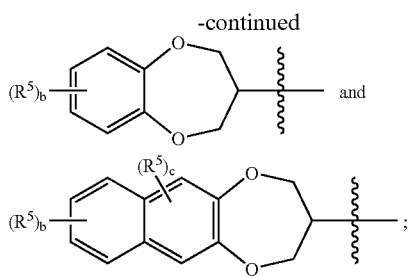 and

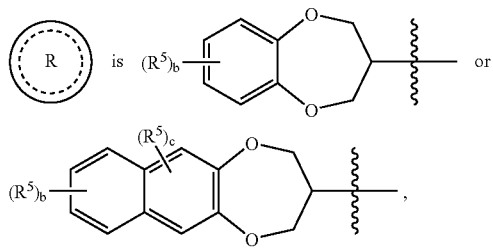;

wherein b is an integer from 0 to 4; and wherein c is an integer from 0 to 2;

each $R^5$ is independently selected from the group consisting of halogen, lower alkyl and nitro;

provided that when

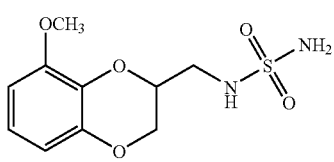

then a is 1;

or a pharmaceutically acceptable salt thereof.

The present invention is further directed to a method for the treatment of epilepsy and related disorders comprising administering to a subject in need thereof, co-therapy with a therapeutically effective amount of one or more anticonvulsant or anti-epileptic agents and a therapeutically effective amount of the compound of formula (II)

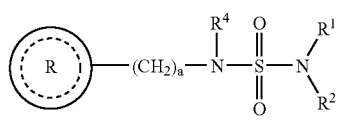 (II)

or a pharmaceutically acceptable salt thereof.

DETAILED DESCRIPTION OF THE INVENTION

The present invention is directed to a method for the treatment of epilepsy and related disorders comprising administering to a subject in need thereof, co-therapy with a therapeutically effective amount of one or more anticonvulsant or anti-epileptic agents and a therapeutically effective amount of a compound of formula (I)

(I)

R—(CH$_2$)$_a$—N(R$^4$)—S(O)$_2$—N(R$^1$)(R$^2$)

or a pharmaceutically acceptable salt thereof, wherein

, a, $R^1$, $R^2$ and $R^4$ are as herein defined.

In preferred embodiments, the present invention is directed to a method for the treatment of epilepsy and related disorders comprising administering to a subject in need thereof, co-therapy with a therapeutically effective amount of one or more anticonvulsant or anti-epileptic agents and a therapeutically effective amount of a compound of formula (I) wherein

, a, $R^1$, $R^2$ and $R^4$ are as hereinafter defined.

In an embodiment of the present invention $R^1$ is selected from the group consisting of hydrogen and methyl. In another embodiment of the present invention $R^2$ is selected from the group consisting of hydrogen and methyl. In yet another embodiment of the present invention $R^1$ and $R^2$ are each hydrogen or $R^1$ and $R^2$ are each methyl.

In an embodiment of the present invention —(CH$_2$)$_a$— is selected from the group consisting of —CH$_2$— and —CH$_2$—CH$_2$—. In another embodiment of the present invention —(CH$_2$)$_a$— is —CH$_2$—.

In an embodiment of the present invention $R^4$ is selected from the group consisting of hydrogen and methyl, preferably, $R^4$ is hydrogen.

In an embodiment of the present invention a is 1.

In an embodiment of the present invention b is an integer from 0 to 2. In another embodiment of the present invention c is an integer from 0 to 2. In another embodiment of the present invention b is an integer from 0 to 1. In another embodiment of the present invention c is an integer from 0 to 1. In yet another embodiment of the present invention the sum of b and c is an integer form 0 to 2, preferably an integer form 0 to 1. In yet another embodiment of the present invention b is an integer from 0 to 2 and c is 0.

In an embodiment of the present invention,

is selected from the group consisting of

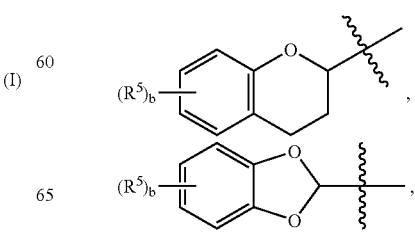

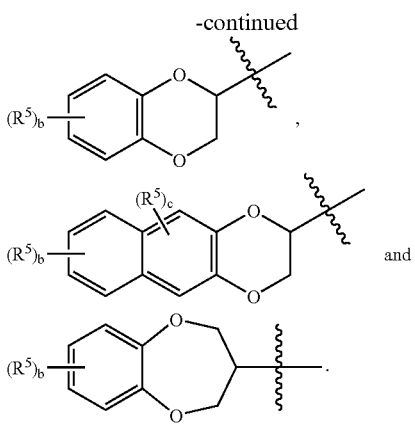

In another embodiment of the present invention,

is selected from the group consisting of

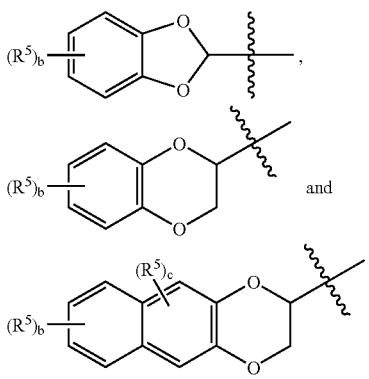

In an embodiment of the present invention,

is selected from the group consisting of 2-(2,3-dihydro-benzo[1,4]dioxinyl), 2-(benzo[1,3]dioxolyl), 3-(3,4-dihydro-benzo[1,4]dioxepinyl), 2-(6-chloro-2,3-dihydro-benzo[1,4]dioxinyl), 2-(6-fluoro-2,3-dihydro-benzo[1,4]dioxinyl), 2-(chromanyl), 2-(5-fluoro-2,3-dihydro-benzo[1,4]dioxinyl), 2-(7-chloro-2,3-dihydro-benzo[1,4]dioxinyl), 2-(6-chloro-benzo[1,3]dioxolyl), 2-(7-nitro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), 2-(8-chloro-2,3-dihydro-benzo[1,4]dioxinyl), 2-(2,3-dihydro-naphtho[2,3-b][1,4]dioxinyl) and 2-(4-methyl-benzo[1,3]dioxolyl).

In another embodiment of the present invention,

is selected from the group consisting 2-(benzo[1,3]dioxolyl), 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl). In another embodiment of the present invention,

is selected from the group consisting of 2-(2,3-dihydro-benzo[1,4]dioxinyl), 2-(7-methyl-2,3-dihydro-benzo[1,4]dioxinyl) and 2-(6-bromo-2,3-dihydro-benzo[1,4]dioxinyl).

In an embodiment of the present invention $R^5$ is selected from the group consisting of halogen and lower alkyl. In another embodiment of the present invention $R^5$ is selected from chloro, fluoro, bromo and methyl.

In an embodiment of the present invention, the stereo-center on the compound of formula (I) is in the S-configuration. In another embodiment of the present invention, the stereo-center on the compound of formula (I) is in the R-configuration.

In an embodiment of the present invention the compound of formula (I) is present as an enantiomerically enriched mixture, wherein the % enantiomeric enrichment (% ee) is greater than about 75%, preferably greater than about 90%, more preferably greater than about 95%, most preferably greater than about 98%.

In an embodiment, the present invention is directed to a method for the treatment of epilepsy and related disorders comprising administering to a subject in need thereof a therapeutically effective amount of one or more anticonvulsant and/or anti-epileptic agents with a compound of formula (I), wherein the compound of formula (I) is (2S)-(–)-N-(6-chloro-2,3-dihydro-benzo[1,4]dioxin-2-ylmethyl)-sulfamide or a pharmaceutically acceptable salt thereof.

Additional embodiments of the present invention, include those wherein the substituents selected for one or more of the variables defined herein (i.e. $R^1$, $R^3$, $R^4$, X—Y and A) are independently selected to be any individual substituent or any subset of substituents selected from the complete list as defined herein.

Representative compounds of the present invention, are as listed in Tables 1 below. Additional compounds of the present invention are as listed in Table 3. In Tables 1 and 2 below, the column headed "stereo" defines the stereo-configuration at the carbon atom of the heterocycle attached at the starred bond. Where no designation is listed, the compound was prepared as a mixture of stereo-configurations. Where an "R" or "S" designation is listed, the stereo-configuration was based on the enantiomerically enriched starting material.

TABLE 1

Representative Compounds of Formula (I)

| ID No. | R | Stereo | (CH$_2$)$_a$ | NR$^4$ | R$^1$ | R$^2$ |
|---|---|---|---|---|---|---|
| 1 | 2-(2,3-dihydro-benzo[1,4]dioxinyl) | | CH$_2$ | NH | H | H |
| 2 | 2-(benzo[1,3]dioxolyl) | | CH$_2$ | NH | H | H |
| 3 | 3-(3,4-dihydro-2H-benzo[1,4]dioxepinyl) | | CH$_2$ | NH | H | H |
| 4 | 2-(2,3-dihydro-benzo[1,4]dioxinyl) | S | CH$_2$ | NH | H | H |
| 5 | 2-(2,3-dihydro-benzo[1,4]dioxinyl) | R | CH$_2$ | NH | H | H |
| 6 | 2-(2,3-dihydro-benzo[1,4]dioxinyl) | | CH$_2$ | NH | methyl | methyl |
| 7 | 2-(2,3-dihydro-benzo[1,4]dioxinyl) | | CH$_2$ | N(CH$_3$) | H | H |
| 8 | 2-(6-chloro-2,3-dihydro-benzo[1,4]dioxinyl) | S | CH$_2$ | NH | H | H |
| 9 | 2-(6-fluoro-2,3-dihydro-benzo[1,4]dioxinyl) | S | CH$_2$ | NH | H | H |
| 10 | 2-(chromanyl) | | CH$_2$ | NH | H | H |
| 13 | 2-(5-fluoro-2,3-dihydro-benzo[1,4]dioxinyl) | S | CH$_2$ | NH | H | H |
| 14 | 2-(7-chloro-2,3-dihydro-benzo[1,4]dioxinyl) | S | CH$_2$ | NH | H | H |
| 15 | 2-(6-chloro-benzo[1,3]dioxolyl) | | CH$_2$ | NH | H | H |
| 16 | 2-(2,3-dihydro-benzo[1,4]dioxinyl) | | CH$_2$CH$_2$ | NH | H | H |
| 18 | 2-(7-nitro-2,3-dihydro-benzo[1,4]dioxinyl) | S | CH$_2$ | NH | H | H |
| 19 | 2-(7-methyl-2,3-dihydro-benzo[1,4]dioxinyl) | S | CH$_2$ | NH | H | H |
| 20 | 2-(5-chloro-2,3-dihydro-benzo[1,4]dioxinyl) | S | CH$_2$ | NH | H | H |
| 22 | 2-(8-methoxy-2,3-dihydro-benzo[1,4]dioxinyl) | S | CH$_2$ | NH | H | H |
| 24 | 2-(6-bromo-2,3-dihydro-benzo[1,4]dioxinyl) | S | CH$_2$ | NH | H | H |
| 29 | 2-(6,7-dichloro-2,3-dihydro-benzo[1,4]dioxinyl) | S | CH$_2$ | NH | H | H |
| 30 | 2-(8-chloro-2,3-dihydro-benzo[1,4]dioxinyl) | S | CH$_2$ | NH | H | H |
| 33 | 2-(2,3-dihydro-naphtho[2,3-b][1,4]dioxinyl) | S | CH$_2$ | NH | H | H |
| 35 | 2-(4-methyl-benzo[1,3]dioxolyl) | | CH$_2$ | NH | H | H |

TABLE 2

Additional Compounds of the Present Invention

| ID No. | Y | Stereo | X | NR$^{14}$ | R$^{11}$ | R$^{12}$ |
|---|---|---|---|---|---|---|
| 23 | 2-(5-methoxy-2,3-dihydro-benzo[1,4]dioxinyl) | S | CH$_2$ | NH | H | H |
| 26 | 2-(6-methylcarbonyl-2,3-dihydro-benzo[1,4]dioxinyl) | S | CH$_2$ | NH | H | H |

TABLE 2-continued

Additional Compounds of the Present Invention

| ID No. | Y | Stereo | X | NR$^{14}$ | R$^{11}$ | R$^{12}$ |
|---|---|---|---|---|---|---|
| 23 | 2-(5-methoxy-2,3-dihydro-benzo[1,4]dioxinyl) | S | CH$_2$ | NH | H | H |
| 32 | 2-(6-methoxycarbonyl-2,3-dihydro-benzo[1,4]dioxinyl) | S | CH$_2$ | NH | H | H |

TABLE 2-continued

Additional Compounds of the Present Invention

| ID No. | Y | Stereo | X | NR¹⁴ | R¹¹ | R¹² |
|---|---|---|---|---|---|---|
| 23 | 2-(5-methoxy-2,3-dihydro-benzo[1,4]dioxinyl) | S | CH₂ | NH | H | H |
| 34 | 2-(6-hydroxymethyl-2,3-dihydro-benzo[1,4]dioxinyl) | S | CH₂ | NH | H | H |
| 36 | 2-(7-amino-2,3-dihydro-benzo[1,4]dioxinyl) | S | CH₂ | NH | H | H |

As used herein, unless otherwise noted, "halogen" shall mean chlorine, bromine, fluorine and iodine.

As used herein, unless otherwise noted, the term "alkyl" whether used alone or as part of a substituent group, includes straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, the notation "*" shall denote the presence of a stereogenic center.

When a particular group is "substituted" (e.g., alkyl, aryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl-alkyl-amino-carbonyl-alkyl" substituent refers to a group of the formula

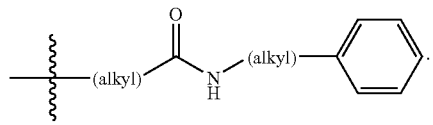

Abbreviations used in the specification, particularly the Schemes and Examples, are as follows:
DCC=Dicyclohexyl Carbodiimide
DCE=Dichloroethane
DCM=Dichloromethane
DIPEA or DIEA=Diisopropylethylamine
DMF=N,N-Dimethylformamide
DMSO=Dimethylsulfoxide
EDC=Ethylcarbodiimide
Et₃N or TEA=Triethylamine
Et₂O=Diethyl ether
EA or EtOAc=Ethyl acetate
EtOH=Ethanol
IPA=2-propanol
Hept=Heptane
HOBT=1-Hydroxybenzotriazole
HPLC=High Pressure Liquid Chromatography
LAH=Lithium Aluminum Hydride
M or MeOH=Methanol
NMR=Nuclear Magnetic Resonance
Pd—C=Palladium on Carbon Catalyst
RP HPLC=Reverse Phase High Pressure Liquid Chromatography
RT or rt=Room temperature
TEA=Triethylamine
TFA=Trifluoroacetic Acid
THF=Tetrahydrofuran
TLC=Thin Layer Chromatography Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

As used herein, unless otherwise noted, the terms "epilepsy and related disorders" or "epilepsy or related disorder" shall mean any disorder in which a subject (preferably a human adult, child or infant) experiences one or more seizures and/or tremors. Suitable examples include, but are not limited to, epilepsy (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, and the like. Preferably, the disorder is selected from epilepsy (regardless of type, underlying cause or origin), essential tremor or restless limb syndrome, more preferably, the disorder is epilepsy (regardless of type, underlying cause or origin) or essential tremor.

The term "subject" as used herein, refers to an animal, preferably a mammal, most preferably a human adult, child or infant, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the symptoms of the disease or disorder being treated; and/or reduction of the severity of one or more of the symptoms of the disease or disorder being treated.

Wherein the present invention is directed to co-therapy or combination therapy, comprising administration of one or more compound(s) of formula (I) and one or more anticonvulsant or anti-epileptic agents, therapeutically effective amount shall mean that amount of the combination of agents taken together so that the combined effect elicits the desired biological or medicinal response. For example, the therapeutically effective amount of co-therapy comprising administration of a compound of formula (I) and at least one suitable anti-epileptic agent would be the amount of the compound of formula (I) and the amount of the suitable anti-epileptic agent that when taken together or sequentially have a combined effect that is therapeutically effective. Further, it will be recognized by one skilled in the art that in the case of co-therapy with a therapeutically effective amount, as in the example above, the amount of the compound of formula (I) and/or the amount of the suitable anti-epileptic agent individually may or may not be therapeutically effective.

As used herein, the terms "co-therapy" and "combination therapy" shall mean treatment of a subject in need thereof by administering one or more anticonvulsant and/or anti-epileptic agent(s) and one or more compounds of formula (I), wherein the compound(s) of formula (I) and the anticonvulsant and/or anti-epileptic agent(s) are administered by any suitable means, simultaneously, sequentially, separately or in a single pharmaceutical formulation. Where the compound(s) of formula (I) and the anticonvulsant and/or anti-epileptic agent(s) are administered in separate dosage forms, the number of dosages administered per day for each compound may be the same or different. The compound(s) of formula (I) and the anticonvulsant and/or anti-epileptic agent(s) may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula (I) and the anticonvulsant and/or anti-epileptic agent(s) may be administered according to simultaneous or alternating regimens, at the same or different times during the course of the therapy, concurrently in divided or single forms.

As used herein, unless otherwise noted, the term "antiepileptic agent" and the abbreviation "AED" will be used interchangeably with the term "anti-convulsant agent," and as used herein, refer to an agent capable of treating, inhibiting or preventing seizure activity or ictogenesis when the agent is administered to a subject or patient.

Suitable examples of anti-convulsant and/or anti-epileptic agents include, but are not limited to:

(a) AMPA antagonists such as AMP-397, E-2007, NS-1209, talampanel, and the like;

(b) Benzodiazepines such as diazepam, lorazepam, clonazepam, clobazam, and the like;

(c) Barbiturates such as phenobarbital, amobarbital, methylphenobarbital, primidone, and the like;

(d) Valproates such as valproic acid, valproate semisodium, valpromide, and the like;

(e) GABA agents such as gabapentin, pregabalin, vigabatrin, losigamone, retigabine, rufinamide, SPD-421 (DP-VPA), T-2000, XP-13512, and the like;

(f) Iminostilbenes such as carbamazepine, oxcarbazepine, and the like;

(g) Hydantoins such as phenytoin sodium, mephenytoin, fosphenytoin sodium, and the like;

(h) NMDA antagonists such as harkoseramide, and the like;

(i) Sodium channel blockers such as BIA-2093, CO-102862, lamotrigine, and the like;

(j) Succinimides such as methsuximide, ethosuximide, and the like; and (k) AEDS such as acetazolamide, clomthiazole edisilate, zonisamide, felbamate, topiramate, tiagabine, levetiracetam, briveracetam, GSK-362115, GSK-406725, ICA-69673, CBD cannabis derivative, isovaleramide (NPS-1776), RWJ-333369, safinamide, seletracetam, soretolide, stiripentol, valrocemide, and the like.

In an embodiment, the anti-convulsant and/or anti-epileptic agent is selected from the group consisting of brivaracetam, carbamazepine, clobazam, clonazepam, ethosuximide, felbamate, gabapentin, lacosamide, lamotrigine, levetiracetam, oxcarbazepine, phenobarbital, phenytoin, pregabalin, primidone, retigabine, rufinamide, safinamide, seletracetam, talampanel, tiagabine, topiramate, valproate, vigabatrin, zonisamide, benzodiazepines, barbiturates and sedative hypnotics.

In another embodiment, the anti-convulsant and/or anti-epileptic agent(s) is selected from the group consisting of carbamazepine, clobazam, clonazepam, ethosuximide, felbamate, gabapentin, lamotrigine, levetiracetam, oxcarbazepine, phenobarbital, phenytoin, pregabalin, primidone, retigabine, rufinamide, talampanel, tiagabine, topiramate, valproate, vigabatrin and zonisamide.

In another embodiment, the anti-convulsant and/or anti-epileptic agent(s) is selected from the group consisting of carbamazepine, lamotrigine, phenobarbital, phenytoin, topiramate, valproate and zonisamide. Preferably, the anti-convulsant and/or anti-epileptic agent(s) is selected from the group consisting of carbamazepine, gabapentin, lamotrigine, levetiracetam, oxcarbazepine, phenytoin, pregabalin, valproate and topiramate. More preferably, the anti-convulsant and/or anti-epileptic is selected from the group consisting of gabapentic, lamotrigine, levetiracetam, valproate and topiramate.

As used herein, the term "composition" is intended to encompass a product comprising the specified ingredients in the specified amounts, as well as any product which results, directly or indirectly, from combinations of the specified ingredients in the specified amounts.

Compounds of formula (I) may be prepared according to the process outlined in Scheme 1.

Accordingly, a suitably substituted compound of formula (X), a known compound or compound prepared by known methods, is reacted with sulfamide, a known compound, preferably wherein the sulfamide is present in an amount in the range of about 2 to about 5 equivalents, in an organic solvent such as THF, dioxane, and the like, preferably at an elevated temperature in the range of about 50° C. to about 100° C., more preferably at about reflux temperature, to yield the corresponding compound of formula (Ia).

Alternatively, a suitably substituted compound of formula (X), a known compound or compound prepared by known methods, is reacted with a suitably substituted compound of formula (XI), a known compound or compound prepared by known methods, in the presence of a base such as TEA, DIPEA, pyridine, and the like, in an organic solvent such as DMF, DMSO, and the like, to yield the corresponding compound of formula (I).

Compounds of formula (X) wherein

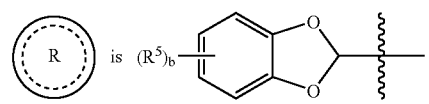

may be prepared according to the process outlined in Scheme 2.

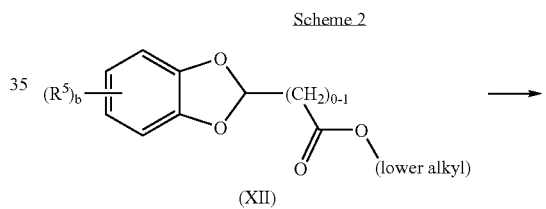

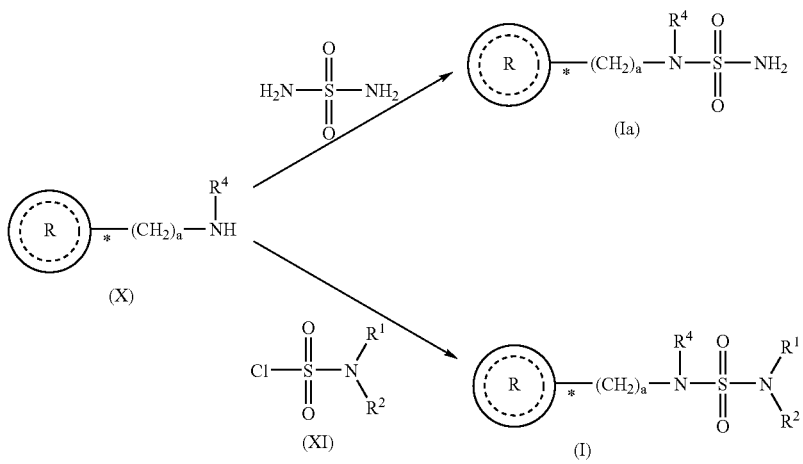

-continued

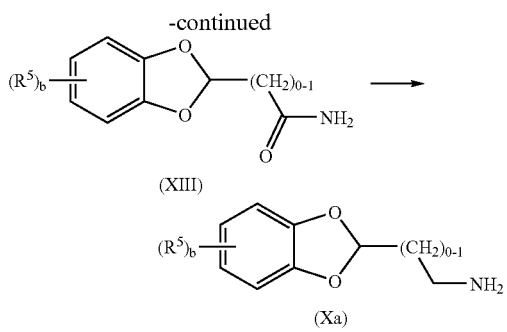

Accordingly, a suitably substituted compound of formula (XII), a known compound or compound prepared by known method (for example as described in Scheme 3 above) is reacted with NH$_4$OH, a known compound, optionally in an organic solvent such as acetonitrile, and the like, to yield the corresponding compound of formula (XIII).

The compound of formula (XIII) is reacted with a suitably selected reducing agent, such as LAH, and the like, and the like, in an organic solvent such as THF, diethyl ether, and the like, to yield the corresponding compound of formula (Xa).

Compounds of formula (X) wherein

is selected from

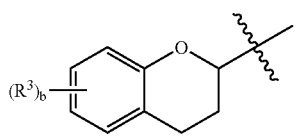

may be prepared according to the process outlined in Scheme 3.

Scheme 3

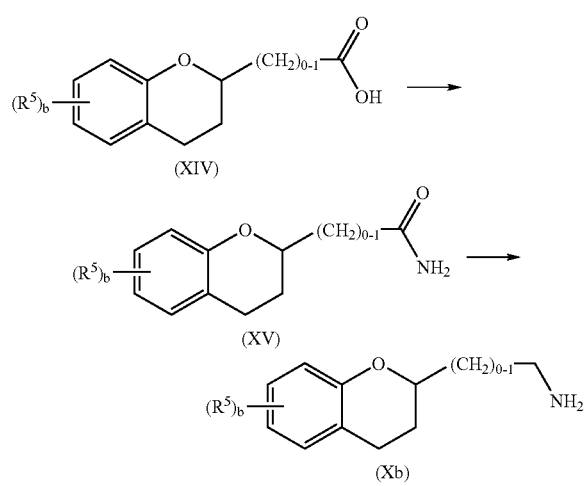

Accordingly, a suitably substituted compound of formula (XIV), a known compound or compound prepared by known methods, is reacted with NH$_4$OH, in the presence of a coupling agent such as DCC, and the like, optionally in an organic solvent such as acetonitrile, and the like, to yield the corresponding compound of formula (XV).

The compound of formula (XV) is reacted with a suitably selected reducing agent, such as LAH, and the like, in an organic solvent such as THF, diethyl ether, and the like, to yield the corresponding compound of formula (Xb).

Compounds of formula (X) wherein

is selected from

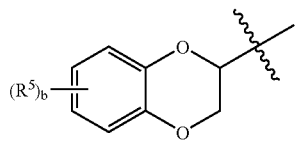

and wherein a is 2, may be prepared according to the process outlined in Scheme 4.

Scheme 5

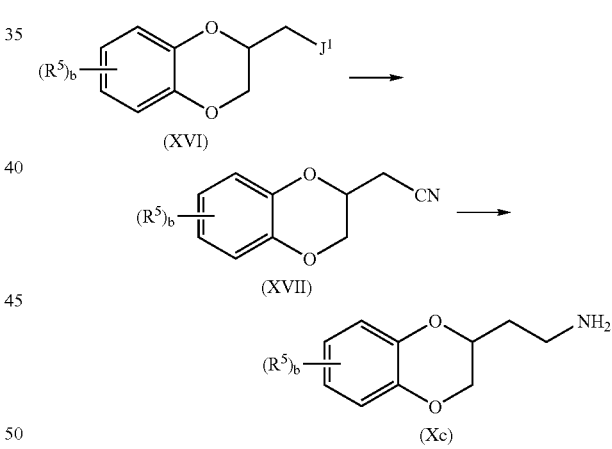

Accordingly, a suitably substituted compound of formula (XVI) wherein J$^1$ is a suitable leaving group such as Br, Cl, I, tosyl, mesyl, triflyl, and the like, a known compound or compound prepared by known methods (for example, by activating the corresponding compound wherein J$^1$ is OH), is reacted with a cyanide such as potassium cyanide, sodium cyanide, and the like, in an organic solvent such as DMSO, DMF, THF, and the like, to yield the corresponding compound of formula (XVII).

The compound of formula (XVII) is reduced according to known methods, for example by reacting with a suitable reducing agent such as LAH, borane, and the like, to yield the corresponding compound of formula (Xc).

Compounds of formula (X) wherein

is selected from

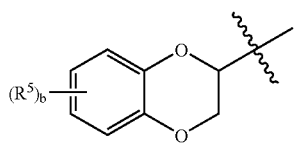

and wherein a is 1, may be prepared according to the process outlined in Scheme 5.

Scheme 5

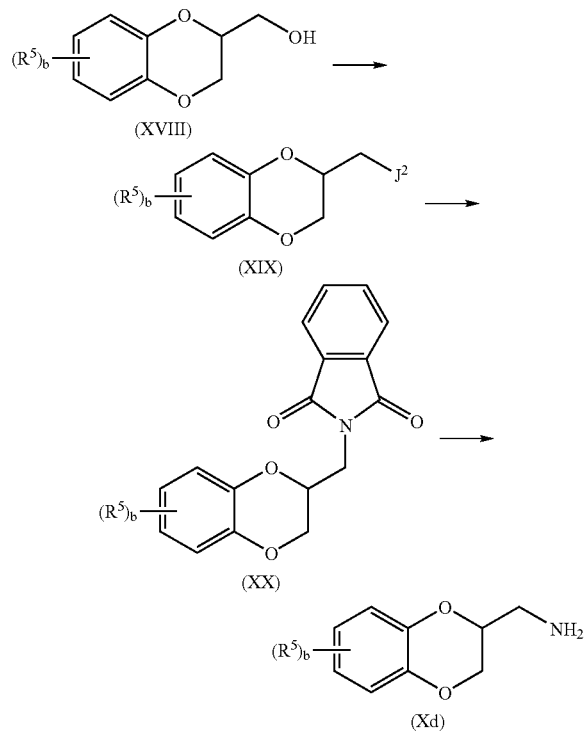

Accordingly, a suitably substituted compound of formula (XVI II), a known compound or compound prepared by known methods is activated, according to known method, to yield the corresponding compound of formula (XIX), wherein $J^2$ is a suitable leaving group, such tosylate, Cl, Br, I, mesylate, triflate, and the like.

The compound of formula (XIX) is reacted with a phthalimide salt such as potassium phthlimide, sodium phthalimide, and the like, in an organic solvent such as DMF, DMSO, acetonitrile, and the like, preferably, at an elevated temperature in the range of from 50° C. to about 200° C., more preferably, at about reflux temperature, to yield the corresponding compound of formula (XX).

The compound of formula (XX) is reacted with $N_2H_4$, a known compound, in an organic solvent such as ethanol, methanol, and the like, preferably, at an elevated temperature in the range of from about 50° C. to about 100° C., more preferably, at about reflux temperature, and the like, to yield the corresponding compound of formula (Xd).

One skilled in the art will recognize that compounds of formula (X) wherein

is selected from

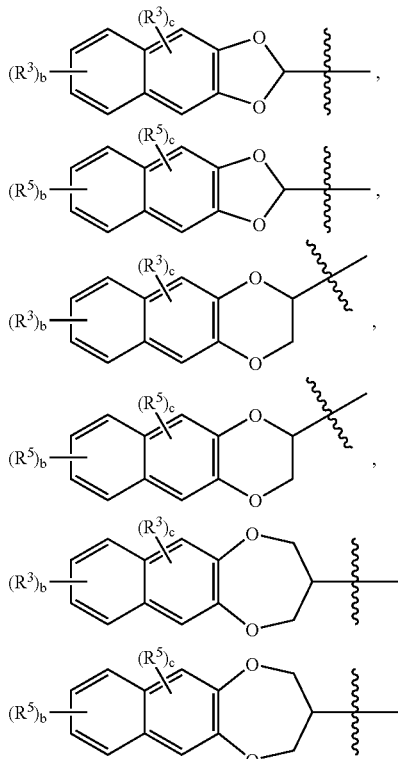

may be similarly prepared according to known methods or for example, according to the processes outlined in Schemes 2 through 5 above, by selecting and substituting the corresponding naphthyl-fused compounds for the benzo-fused starting materials.

One skilled in the art will further recognize that wherein a single enantiomer (or a mixture of enantiomers wherein one enantiomer is enriched) of a compound of formula (X) is desired, the above processes as described in Schemes 1 through 5 may be applied by substituting the corresponding single enantiomer (or mixture of enantiomers wherein one enantiomer is enriched) for the appropriate starting material.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention provides methods of treating epilepsy and related disorders, regardless of underlying cause and stage of development, comprising administering to a subject in need thereof, co-therapy with a therapeutically effective amount of one or more anticonvulsant or anti-epileptic agents and a therapeutically effective amount of a compound of formula (I) as described herein. The methods of this invention therefore provide the ability to suppress seizures, convulsions or the symptoms of an analogous seizure related disorder. In order to accomplish this objective the compounds or compositions of this invention must be used in the correct therapeutically effective amount or dose, as described below.

Optimal dosages and schedules to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The present invention further comprises pharmaceutical compositions containing one or more compounds of formula (I) and one or more anti-convulsant and/or anti-epileptic agents with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more of the compounds of formula (I) and more or more of the anticonvulsant and/or anti-epileptic agents, as the active ingredients are intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.01-200.0 mg/kg/day, preferably from about 0.1 to 100 mg/kg/day, more preferably from about 0.5-50 mg/kg/day, more preferably from about 1.0-25.0 mg/kg/day or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the active compound(s), and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of epilepsy or related disorders is required.

The daily dosage of the products may be varied over a wide range from 0.01 to 200 mg/kg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 150.0 mg/kg of body weight per day or any range therein. Preferably, the range is from about 0.1 to about 100.0 mg/kg of body weight per day, more preferably, from about 0.5 mg/kg to about 50 mg/kg, more preferably, from about 1.0 to about 25.0 mg/kg of body weight per day. The compounds may be administered on a regimen of 1 to 4 times per day.

Therapeutically effective dosage levels and dosage regimens for the anti-convulsant and anti-epileptic agents disclosed herein, may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http://www.pdrel.com) and other sources.

One skilled in the art will recognize that a therapeutically effective dosage of the compounds of the present invention can include repeated doses within a prolonged treatment regimen that will yield clinically significant results.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

Determination of effective dosages is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

The following Examples are set forth to aid in the understanding of the invention, and are not intended and should not be construed to limit in any way the invention set forth in the claims which follow thereafter.

EXAMPLE 1

((3,4-Dihydro-2H-benzo[b][1,4]dioxepin-3-yl)methyl)sulfamide (Compound #3)

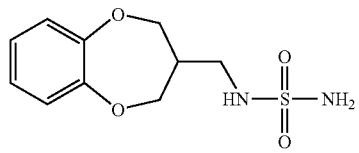 [SMILES: NS(=O)(=O)NCC1COc2ccccc2OC1]

Catechol (5.09 g, 46.2 mmol) and potassium carbonate were combined in acetonitrile and heated to reflux for one hour. 2-Chloromethyl-3-chloro-1-propene (5.78 g, 46.2 mmol) was added and the reaction was continued at reflux for 24 hours. The solution was cooled to room temperature and filtered. The filtrate was evaporated and the residue was diluted with water and extracted with diethyl ether (3×). The combined organic solution was dried over $MgSO_4$ and concentrated. Chromatography (2% ethyl ether in hexane) yielded 3-methylene-3,4-dihydro-2H-benzo[b][1,4]dioxepine as a colorless oil.

MS (ESI): 163.2 $(M+H^+)$
$^1$H NMR (300 MHz, $CDCl_3$), δ: 6.94 (m, 4H), 5.07 (s, 2H), 4.76 (s, 4H).

3-Methylene-3,4-dihydro-2H-benzo[b][1,4]dioxepine (5.00 g, 30.8 mmol) was dissolved in dry THF (100 mL). Borane-THF (1.0 M in THF, 10.3 mL) was added at 0° C. The reaction was stirred at RT for 5 hours. Aminosulfonic acid (6.97 g, 61.6 mmol) was added. The reaction was heated to reflux overnight. The reaction was cooled to room temperature and aqueous sodium hydroxide (3.0 M, 100 mL) was added. The solution was extracted with ethyl acetate (3×100 mL). The combined organic solution was dried over $MgSO_4$. The solution was concentrated under vacuum and purified by chromatography (2% to 8% methanol in dichloromethane) to yield ((3,4-dihydro-2H-benzo[b][1,4]dioxepin-3-yl)methyl) amine as a colorless oil.

MS (ESI): 180.1 $(M+H^+)$
$^1$H NMR (300 MHz, DMSO), δ: 6.92 (m, 4H), 4.21 (m, 2H), 4.07 (m, 2H), 3.33 (broad, 2H), 3.16 (d, J=4 Hz, 1H), 2.72 (d, J=4 Hz, 1H), 2.30 (m, 1H).

((3,4-Dihydro-2H-benzo[b][1,4]dioxepin-3-yl)methyl) amine (2.90 g, 16.2 mmol) and sulfamide (3.11 g, 32.4 mmol) were combined in dry dioxane (60 ml) and heated to reflux overnight. Chloroform was added and the precipitate was removed by filtration. The filtrate was concentrated under vacuum and purified by chromatography (2% to 8% acetone in dichloromethane) to yield the title compound as an off-white solid.

258.8 $(M+H^+)$
$^1$H NMR (300 MHz, DMSO), δ: 6.92 (m, 4H), 6.71 (broad, 1H), 6.59 (broad, 2H), 4.19 (m, 2H), 4.04 (m, 2H), 3.00 (m, 2H), 2.39 (m, 1H).

EXAMPLE 2

N-(2,3-Dihydro-benzo[1,4]dioxin-2-ylmethyl)-sulfamide (Compound #1)

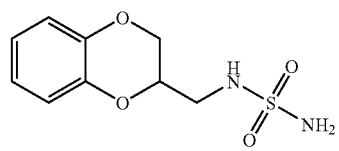 [SMILES: NS(=O)(=O)NCC1COc2ccccc2O1]

Racemic 2,3-dihydro-1,4-benzdioxin-2-ylmethylamine (4.4 g, 26 mmol) and sulfamide (5.1 g, 53 mmol) were combined in 1,4 dioxane (100 mL) and refluxed for 2 h. The reaction was cooled to room temperature and a small amount of solid was filtered and discarded. The filtrate was evaporated in vacuo and the residue was purified using flash column chromatography (DCM:Methanol—10:1) to yield a white solid. The solid was recrystallized from DCM to yield the title compound as a white solid.

mp: 97.5-98.5° C.
Elemental Analysis:
Anal Calc: C, 44.25; H, 4.95; N, 11.47; S, 13.13
Anal Found: C, 44.28; H, 4.66; N, 11.21; S, 13.15
$H^1$ NMR (DMSO d6) 6 6.85 (m, 4H), 6.68 (bd s, 3H, NH), 4.28 (m, 2H), 3.97 (dd, J=6.9, 11.4 Hz, 1H), 3.20 (m, 1H), 3.10 (m, 1H).

EXAMPLE 3

(Benzo[1,3]dioxol-2-ylmethyl)sulfamide (Compound #2)

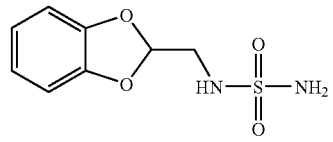 [SMILES: NS(=O)(=O)NCC1Oc2ccccc2O1]

Catechol (10.26 g, 93.2 mmol), sodium methoxide (25% by weight in methanol, 40.3 g, 186 mmol), and methyl dichloroacetate (13.3 g, 93.2 mmol) were combined in dry methanol (100 mL). The solution was heated to reflux overnight. The reaction was cooled to room temperature, acidified by addition of concentrated hydrochloric acid and then reduced in volume under vacuum to about 50 mL. Water was added and the mixture was extracted with diethyl ether (3×100 mL). The combined organic solution was dried with $MgSO_4$, concentrated to a brown solid, and chromatographed (2% ethyl acetate in hexane) to yield benzo[1,3]dioxole-2-carboxylic acid methyl ester as a colorless oil.

MS (ESI): 195.10 $(M+H^+)$
$^1$H NMR (300 MHz, $CDCl_3$), δ: 6.89 (broad, 4H), 6.29 (s, 1H), 4.34 (q, J=7 Hz, 2H), 1.33 (t, J=7 Hz, 3H).

To benzo[1,3]dioxole-2-carboxylic acid methyl ester (7.21 g, 40.0 mmol) was added ammonium hydroxide (29% in water, 10 mL) and enough acetonitrile to make the mixture homogeneous (~5 mL). The solution was stirred for two hours at room temperature and then distilled water was added. Benzo[1,3]dioxole-2-carboxylic acid amide precipitated as a white solid and was collected by filtration and used without further purification.

MS (ESI): 160.00 (M+H$^+$)

$^1$H NMR (300 MHz, DMSO), δ: 7.99 (s, broad, 1H), 7.72 (s, broad, 1H), 6.94 (m, 2H), 6.86 (m, 2H), 6.30 (s, 1H).

Benzo[1,3]dioxole-2-carboxylic acid amide (5.44 g, 32.9 mmol) was dissolved in tetrahydrofuran (THF, 100 mL). Lithium aluminum hydride (LAH, 1M in THF, 39.5 mL, 39.5 mmol) was added slowly to the solution at room temperature. The reaction was stirred at room temperature for 24 hours. Distilled water was added to destroy the excess LAH. Aqueous sodium hydroxide (3.0 M, 100 mL) was added and the solution was extracted with ethyl acetate (3×100 mL). The combined organic solution was washed with water and dried over MgSO$_4$. The solvent was evaporated to yield C-benzo[1,3]dioxol-2-yl-methylamine as a colorless oil.

MS (ESI): 152.1 (M+H$^+$)

$^1$H NMR (300 MHz, CDCl$_3$), δ: 6.87 (m, 4H), 6.09 (t, J=4 Hz, 1H), 3.13 (d, J=4 Hz, 2H).

C-Benzo[1,3]dioxol-2-yl-methylamine (2.94 g, 19.4 mmol) and sulfamide (3.74 g, 38.9 mmol) were combined in dry dioxane (50 mL) and the solution was heated to reflux overnight. The reaction was concentrated and the residue was chromatographed (2% to 10% acetone in dichloromethane) to yield the title compound as a white solid.

MS (ESI): 230.0 (M+H$^+$)

$^1$H NMR (300 MHz, CDCl$_3$), δ: 6.87 (m, 4H), 6.25 (t, J=4 Hz, 1H), 4.79 (broad, 1H), 4.62 (broad, 1H), 3.64 (d, J=4 Hz, 2H).

EXAMPLE 4

(2S)-(−)-N-(2,3-Dihydro-benzo[1,4]dioxin-2-ylmethyl)-sulfamide (Compound #4)

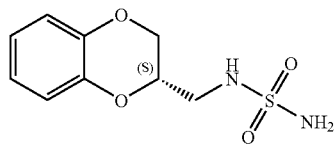

Catechol (13.2 g, 0.12 mol) and potassium carbonate (16.6 g, 0.12 mol) were stirred in DMF (250 mL) and (2R)-glycidyl tosylate (22.8 g, 0.10 mol) was added and the reaction was stirred at 60° C. for 24 h. The reaction was cooled to room temperature and diluted with ice water (1 L) and extracted with diethyl ether (4 times). The combined organic solution was washed 3 times with 10% potassium carbonate, once with water, once with brine and evaporated in vacuo to yield a white solid which was purified by flash column chromatography (DCM:Methanol—50:1) to yield ((2S)-2,3-dihydro-benzo[1,4]dioxin-2-yl)-methanol as a solid.

The solid (13.3 g, 68 mmol) was dissolved in pyridine (85 mL) cooled to 0° C., p-toluenesulfonyl chloride (13.0 g, 68 mmol) was added and the reaction mixture stirred at room temperature for 20 h. The reaction was diluted with diethyl ether (1 L) and 1 N HCl (1.2 L). The organic layer was separated and washed 2 times with 1 N HCl (500 mL), 4 times with water (150 mL), once with brine, dried (MgSO$_4$) and evaporated in vacuo to yield a white solid which was purified by flash column chromatography (Hept:EA—2:1) to yield toluene-4-sulfonic acid (2S)-2,3-dihydro-benzo[1,4]dioxin-2-ylmethyl ester as a white solid.

The white solid was combined with potassium phthalimide (14.4 g, 78 mmol) in DMF (250 mL) and heated to reflux for 1 h, cooled to room temperature and poured into vigorously stirring water (1.5 L) and stirred 30 min. White solid was filtered and the solid was washed several times with water, 2% NaOH, and water again and let air dry to yield a (2S)-2-(2,3-Dihydro-benzo[1,4]dioxin-2-ylmethyl)-isoindole-1,3-dione as white powdery solid.

The powdery white solid was combined with hydrazine (2.75 g, 86 mmol) in EtOH (225 mL) and heated at reflux for 2 h, cooled to room temperature and 1N HCl added to pH 1.0 and stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried (Na$_2$SO$_4$) and evaporated in vacuo to a yield a light yellow oil. The oil was purified by flash column chromatography (DCM:MeOH—10:1) to yield an oil. A portion of the oil (4.82 g, 29 mmol) in 2-propanol (250 mL) was treated with 1N HCl (30 mL) and heated on steambath until homogeneous and then let cool to room temperature. After 3 h, the mixture was ice cooled for 2 h. A white flaky solid (the corresponding HCl salt of (2S)-C-(2,3-Dihydro-benzo[1,4] dioxin-2-yl)-methylamine) was filtered off and then recrystallized again from 2-propanol to yield a white solid.

$[E]_D$=−69.6 (c =1.06, EtOH).

The white solid was partitioned between DCM and dilute NaOH, and the DCM was dried (NaSO$_4$) and evaporated in vacuo to yield (2S)-C-(2,3-Dihydro-benzo[1,4]dioxin-2-yl)-methylamine as an oil.

$[\alpha]_D$=−57.8 (c=1.40, CHCl$_3$).

The oil (2.1 g, 12.7 mmol) and sulfamide (2.44 g, 25.4 mmol) were refluxed in dioxane (75 mL) for 2 h and the crude product was purified by flash column chromatography (DCM:MeOH 10:1) to yield a white solid, which was recrystallized from DCM to yield the title compound as a white crystalline solid.

mp 102-103° C.

$[\alpha]_D$=−45.10 (c=1.05, M);

$^1$H NMR (DMSOd6), δ 6.86 (m, 4H), 6.81 (bd s, 3H, NH), 4.3 (m, 2H), 3.97 (dd, J=6.9, 11.4 Hz, 1H), 3.20 (dd, J=5.5, 13.7 Hz, 1H), 3.10 (dd, J=6.9, 13.7 Hz, 1H).

Elemental Analysis:

Anal Calc: C, 44.25; H, 4.95; N, 11.47; S, 13.13 Anal Found: C, 44.20; H, 4.69; N, 11.40; S, 13.22.

EXAMPLE 5

N-(2,3-Dihydro-benzo[1,4]dioxin-2-ylmethyl)-N', N'dimethylsulfamide (Compound #6)

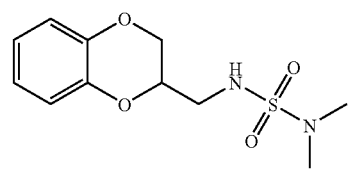 [SMILES: CN(C)S(=O)(=O)NCC1COc2ccccc2O1]

Racemic 2,3-dihydro-1,4-benzdioxin-2-ylmethylamine (8.25 g, 5.0 mmol) and triethylamine (1.52 g, 15 mmol) were combined in DMF (10 mL) and cooled in an ice bath as dimethylsulfamoyl chloride (1.44 g, 10 mmol) was added. The reaction mixture was then stirred for 3 hr with continued cooling. The reaction mixture was partitioned between ethyl acetate and water, and the ethyl acetate solution was washed with brine, dried (MgSO$_4$) and evaporated in vacuo to yield an oil. The oil was purified using flash column chromatography (ethyl acetate:Heptane—1:1) to yield a white solid, which was recrystallized (ethyl acetate/Hexane) to yield the title compound as a white floccular solid.

mp 76-78° C.

MS 273 (MH$^+$).

Elemental Analysis:

Anal Calc: C, 48.52; H, 5.92; N, 10.29; S, 11.78

Anal Found: C, 48.63; H, 5.62; N, 10.20; S, 11.90

$^1$H NMR (CDCl$_3$), δ 6.87 (m, 4H), 4.59 (bd m, 1H, NH), 4.35 (m, 1H), 4.27 (dd, J=2.3, 11.4 Hz, 1H), 4.04 (dd, J=7.0, 11.4, 1H), 3.36 (m, 2H), 2.82 (s, 6H).

EXAMPLE 6

N-(2,3-Dihydro-benzo[1,4]dioxin-2-ylmethyl)-N-methylsulfamide (Compound #7)

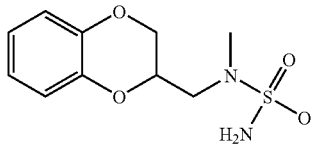

Racemic 2,3-dihydro-1,4-benzdioxin-2-ylmethylamine (825 mg, 5 mmol) was dissolved in ethyl formate (15 mL), refluxed for 30 min and evaporated in vacuo to yield N-(2,3-dihydro-benzo[1,4]dioxin-2-ylmethyl)-formamide as an oil.

The oil in diethyl ether (25 mL) was treated with 1M LAH in THF (9.0 mL, 9.0 mmol) at 0° C. and stirred for 5 h at room temperature. The reaction was cooled in an ice bath and quenched with water (0.50 mL), followed by 3 N NaOH (0.50 mL) and water (0.50 mL). The mixture was then stirred at room temperature for 1 h. Solid was filtered and the filtrate was evaporated in vacuo to yield a residue which was partitioned between 1N HCl and diethyl ether. The aqueous phase was basified with 1N NaOH and extracted with diethyl ether. The organic phase was dried (MgSO$_4$) and evaporated in vacuo to yield (2,3-dihydro-benzo[1,4]dioxin-2-ylmethyl)-methyl-amine as an oil.

MS 180 (MH$^+$)

$^1$H NMR (CDCl$_3$), δ 6.85 (m, 4H), 4.30 (m, 2H), 4.02 (dd, J=7.9, 11.6 Hz, 1H), 2.85 (m, 2H), 2.50 (s, 3H)

The oil (380 mg, 2.1 mmol) and sulfamide (820 mg, 8.5 mmol) were combined in dioxane (15 mL), refluxed for 1.5 h and evaporated in vacuo to yield a crude residue. The residue was purified via column chromatography (ethyl acetate/Heptane 1:1 ) and the resultant solid was recrystallized from ethyl acetate/Hexane to yield the title compound as a white solid.

mp 97-98° C.

MS 257 (M$^{-1}$).

Elemental Analysis:

Anal Calc: C, 46.50; H, 5.46; N, 10.85; S, 12.41

Anal Found: C, 46.48; H, 5.65; N, 10.90; S, 12.07

$^1$H NMR (CDCl$_3$) δ 6.86 (m, 4H), 4.52 (bs, 2H), 4.46 (m, 1H), 4.29 (dd, J=2.3, 11.5 Hz, 1H), 4.05 (dd, J=6.5, 11.5 Hz, 1H), 3.51 (dd, J=6.7, 14.9 Hz, 1H), 3.40 (dd, J=5.9, 14.9 Hz, 1H), 2.99 (s, 3H).

EXAMPLE 7

(2S)-(−)-N-(6-Chloro-2,3-dihydro-benzo[1,4]dioxin-2-ylmethyl)-sulfamide (Compound #8)

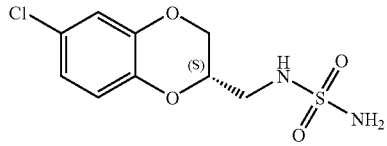

Following the procedure outlined in Example 4 above, 4-chlorocatechol was reacted to yield a mixture of (2S)-C-(7-Chloro-2,3-dihydro-benzo[1,4]dioxin-2-yl)-methylamine and (2S)-C-(6-Chloro-2,3-dihydro-benzo[1,4]dioxin-2-yl)-methylamine (ca. 3:1 ratio of 6-chloro:7-chloro isomers by RP HPLC).

The mixture was dissolved in 2-propanol (100 mL) and 1N HCl in diethyl ether was added until pH=1.0 was attained. The hydrochloride salt that precipitated was filtered (2.65 g) and re-crystallized from methanol/IPA to yield white crystals. The white crystals were partitioned between DCM and dilute NaOH. The DCM was dried and evaporated in vacuo to yield purified (2S)-C-(6-Chloro-2,3-dihydro-benzo[1,4]dioxin-2-yl)-methylamine as an oil.

$[\alpha]_D$=−67.8 (c=1.51, CHCl$_3$).

The oil (7.75 mmol) and sulfamide (1.50 g, 15.5 mmol) were combined in dioxane (50 mL) and refluxed for 2.0 h, cooled to room temperature and evaporated in vacuo to yield a solid. The product was purified via flash column using DCM/methanol 20:1 to yield the title compound as a white solid.

MS 277 (M$^{-1}$)

$[\alpha]_D$=−59.9° (c=1.11, M)

$^1$H NMR (CDCl$_3$), δ 6.90 (d, J=2.2 Hz, 1H), 6.81 (m, 2H), 4.76 (m, 1H), 4.55 (s, 2H), 4.40 (m, 1H), 4.29 (dd, J=2.4, 11.5 Hz, 1H), 4.05 (dd, J=7.1, 11.5 Hz, 1H), 3.45 (m, 2H)

Elemental Analysis:

Anal Calc: C, 38.78; H, 3.98; N, 10.05

Anal Found: C, 38.80; H, 3.67; N, 9.99.

The filtrates of the crystallized hydrochloride salt of (2S)-C-(6-Chloro-2,3-dihydro-benzo[1,4]dioxin-2-yl)-methylamine prepared above were recovered (ca. 1:1 of 6-chloro:7-chloro isomers) and evaporated in vacuo to yield a solid, which was partitioned between DCM (200 mL) and dilute NaOH (0.5 M, 50 mL). The DCM solution was washed once with brine, dried (Na$_2$SO$_4$) and evaporated in vacuo to yield an oil, which was purified via reverse phase HPLC (10-50% ACN with 0.16% TFA in water with 0.20% TFA) to yield (2S)-C-(7-Chloro-2,3-dihydro-benzo[1,4]dioxin-2-yl)-methylamine as a residue.

The residue was combined with sulfamide (0.90 g, 9.4 mmol) in dioxane (25 mL) and refluxed for 2.5 h, cooled to room temperature and evaporated in vacuo to yield an oil. The oil was purified by flash column chromatography using DCM/methanol—10:1 to yield (2S)-(−)-N-(7-Chloro-2,3-dihydro-benzo[1,4]dioxin-2-ylmethyl)-sulfamide as a white solid.

MS 277 (M⁻¹)

¹H NMR (CDCl₃/CD₃OD), δ 6.88 (d, J=0.7 Hz, 1H), 6.81 (m, 2H), 4.37 (m, 1H), 4.30 (dd, J=2.3, 11.6 Hz, 1H), 4.04 (dd, J=7.0, 11.6 Hz, 1H), 3.38 (m, 2H).

EXAMPLE 8

Chroman-2-ylmethylsulfamide (Compound #10)

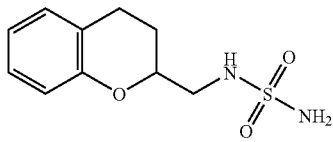 [SMILES: NS(=O)(=O)NCC1CCc2ccccc2O1]

Chroman-2-carboxylic acid (4.5 g, 25 mmol) and HOBT (3.86 g, 25 mmol) were combined in DCM (40 mL) and DMF (10 mL). Dimethylaminopropyl ethylcarbodiimide (EDC, 4.84 g, 25 mmol) was added at room temperature and the reaction mixture was stirred for 30 min. Ammonium hydroxide (2.26 mL, 33.4 mmol) was added and the reaction mixture was stirred for 16 h. The reaction mixture was diluted with DCM (50 mL) and water (50 mL) and the pH of the mixture was adjusted to about pH=3.0 with 1 N HCl. The DCM was separated and the aqueous phase extracted twice with DCM. The combined DCM phase was dried (Na₂SO₄) and evaporated in vacuo to yield an oil, which was purified with flash column chromatography (ethyl acetate) to yield an oil.

The oil (5.35 g, 30 mmol) in THF (90 mL) was stirred as 1M LAH in THF (36 mL, 36 mmol) was added and the reaction mixture was then stirred at room temperature for 20 h. The reaction was quenched with water, stirred for 2 hours, the solution decanted, dried (Na₂SO₄) and evaporated in vacuo to yield C-chroman-2-yl-methylamine as an oily amine.

The oily amine (1.63 g, 10 mmol) and sulfamide (1.92 g, 20 mmol) were combined in dioxane (50 mL) and brought to reflux for 2 h. The solution was cooled and evaporated in vacuo to yield an oil, which was purified via column chromatography (DCM:Methanol 10:1) to yield a white solid. The solid was recrystallized from ethyl acetate/hexane to yield chroman-2-ylmethylsulfamide as a white solid.

mp 100-101° C
MS 241 (M⁻¹).
Elemental Analysis:
Anal Calc: C, 49.57; H, 5.82; N, 11.56; S, 13.23
Anal Found: C, 49.57; H, 5.80; N, 11.75; S, 13.33.

EXAMPLE 9

2-(2,3-Dihydro-benzo[1,4]dioxin-2-yl)-ethylsulfamide (Compound #16)

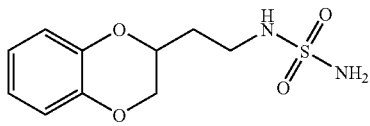 [SMILES: NS(=O)(=O)NCCC1COc2ccccc2O1]

Potassium cyanide (2.05 g, 31.5 mmol) was added to 2-bromomethyl-(2,3dihydrobenzo[1,4]dioxine) (6.87 g, 30 mmol) in DMSO (90 mL) and stirred at ambient temperature for 20 h. The reaction mixture was then diluted with water (250 mL) and extracted twice with diethyl ether. The diethyl ether was washed with water, then washed twice with brine, dried (Na₂SO₄) and evaporated in vacuo to yield 2-cyanomethyl-(2,3dihydrobenzo[1,4]dioxine) as a white solid.

¹H NMR (CDCl₃), δ 6.89 (m, 4H), 4.50 (m, 1H), 4.31 (dd, J=2.3, 11.5 Hz, 1H), 4.08 (dd, J=6.2, 11.6 Hz, 1H), 2.78 (d, J=6.1, Hz, 2H).

The 2-cyanomethyl-(2,3dihydrobenzo[1,4]dioxine) was dissolved in THF (50 mL) and 1 M BH₃ in THF (80 mL, 80 mmol) was added and the reaction mixture refluxed for 5 h, then stirred at ambient temperature for 1 6h. With ice bath cooling, 2N HCl was added until pH=1.0 was achieved. The reaction mixture was then stirred for 1 h at room temperature and evaporated in vacuo to yield an oil. The oil was partitioned between 3N NaOH and diethyl ether, and the diethyl ether solution was washed with brine, dried (Na₂SO₄) and evaporated in vacuo to yield crude 2-(2,3 dihydrobenzo[1,4] dioxin-2-yl)ethylamine.

MS (M+H)⁺ 180.

The crude 2-(2,3 dihydrobenzo[1,4]dioxin-2-yl)ethylamine in dioxane (100 mL) was combined with sulfamide (3.0 g, 31 mmol) and heated to reflux for 2 h. The solution was cooled and evaporated in vacuo to yield an orange solid, which was purified by column chromatography (DCM:MeOH—10:1) to yield a white solid. The solid was re-crystallized from DCM to yield the title compound as a solid.

MS (M-1) 257
MP 101-103° C. (corr)
¹H NMR (CDCl₃): δ 6.86 (m, 4H), 4.70 (m, 1H), 4.52 (s, 2H), 4.30 (m, 2H), 3.94 (dd, J=7.4, 11.3 Hz, 1H), 3.43 (dd, J=6.4, 12.9 Hz, 2H), 1.94 (dd, J=6.5, 12.9, 2H).
Elemental Analysis:
Measured: C, 46.48; H, 5.60; N, 10.81; S, 12.41 Calculated: C, 46.50; H, 5.46; N, 10.85; S, 12.41

EXAMPLE 10

(2S)-(−)-N-(6,7Dichloro-2,3-dihydro-benzo[1,4] dioxin-2-ylmethyl)-sulfamide (Compound #29)

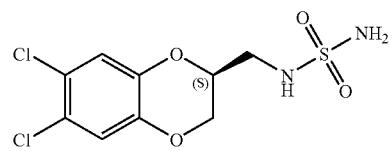

4,5 Dichloroatechol (8.6 g, 48 mmol) and potassium carbonate (6.64 g, 48 mmol) were stirred in DMF (200 mL). (2R)-Glycidyl tosylate (9.12 g, 40 mmol) was added and the reaction mixture was stirred at 60° C. for 24 h. The reaction mixture was cooled to room temperature and then diluted with ice water (600 mL) and extracted with diethyl ether (4 times). The combined organic solution was washed 3 times with 10% potassium carbonate, twice with brine, dried (MgSO₄) and evaporated in vacuo to yield a viscous oil of (2S)-2-(6,7-dichloro-2,3-dihydro-benzo[1,4]dioxine) methanol.

The (2S)-2-(6,7 dichloro-2,3-dihydro-benzo[1,4]dioxine) methanol oil (6.4 g, 27 mmol) was dissolved in pyridine (50 mL) cooled to 0° C. Then, p-toluenesulfonyl chloride (5.2 g, 27 mmol) was added and the reaction mixture was stirred at room temperature for 20 h. The reaction mixture was diluted with diethyl ether and 1N HCl (750 mL) and the organic layer was separated and washed 2 times with 1N HCl (250 mL), once with water (150 mL), twice with brine, dried (MgSO₄) and evaporated in vacuo to yield light yellow solid of toluene-4-sulfonic acid (2S)-6,7-dichloro-2,3-dihydro-benzo[1,4]dioxin-2-ylmethyl ester.

¹H NMR (CDCl3): δ 7.79 (d, J=8.3 Hz, 2H), 7.36 (d, J=8.0 Hz, 2H), 6.94 (s, 1H), 6.83 (s, 1H), 4.37 (m, 1H), 4.2 (m, 3H), 4.03 (dd, J=6.3, 11.7 Hz, 1H), 2.47 (s, 3H).

Toluene-4-sulfonic acid (2S)-6,7-dichloro-2,3-dihydro-benzo[1,4]dioxin-2-ylmethyl ester (8.0 g, 20.5 mmol) was combined with potassium phthalimide (6.1 g, 33 mmol) in DMF (75 mL) and heated to reflux for 1 h, cooled to room temperature and poured into vigorously stirring water (0.5 L) and then stirred 30 min. White solid was filtered and the solid was washed several times with water, 2% NaOH, and water again and then let air dry to yield (2S)-2-(6,7-dichloro-2,3-dihydro-benzo[1,4]dioxin-2-ylmethyl)-isoindole-1,3-dione (6.0 g, 80%) as a white powdery solid.

The white powdery solid was combined with hydrazine (1.06 g, 33 mmol) in EtOH (80 mL) and heated at reflux for 2 h, then cooled to room temperature. 1 N HCl was added to adjust the reaction mixture's pH to pH 1.0 and the reaction mixture was then stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried (Na₂SO₄) and evaporated in vacuo to a yield a viscous oil of (2S)-2-aminomethyl-(6,7-dichloro-2,3-dihydro-benzo[1,4]dioxine).

¹H NMR (CDCl3): δ 6.98 (s, 1H), 6.96 (s, 1H), 4.25 (dd, J=2.0, 11.2 Hz, 1H), 4.15 (m, 1H), 4.0 (m, 1H), 2.97 (d, J=5.5 Hz, 2H).

A portion of the oil (3.8 g, 16 mmol) and sulfamide (3.1 g, 32.4 mmol) were refluxed in dioxane (100 mL) for 2 h and the crude product was purified by flash column chromatography (DCM:MeOH 20:1) to yield the title compound as a white solid, which was recrystallized from ethyl acetate/hexane to yield the title compound as a white crystalline solid.

MS [M−H]⁻ 311.0
mp 119-121° C.
[α]$_D$=−53.4° (c=1.17, M)
¹H NMR (DMSOd6): δ 7.22 (s, 1H), 7.20 (s, 1H), 6.91 (bd s, 1H), 6.68 (bd s, 2H), 4.35 (m, 2H), 4.05 (dd, J=6.5, 11.5 Hz, 1H), 3.15 (m, 2H).
Elemental Analysis:
Elemental Analysis:
Measured: C, 34.52; H, 3.22; N, 8.95; Cl, 22.64; S, 10.24
Calculated: C, 34.64; H, 2.68; N, 8.87; Cl, 22.94; S, 10.35.

EXAMPLE 11

(2S)-(−)-N-(7-Amino-2,3-dihydro-benzo[1,4]dioxin-2-ylmethyl)-sulfamide (Compound #36)

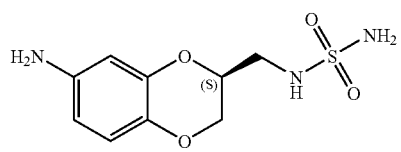

(2S)-(−)-N-(2,3-Dihydro-7-nitro-benzo[1,4]dioxin-2-yl-methyl)-sulfamide (1.2 g, 4.15 mmol), was prepared from 4-nitrocatechol according to the process outlined in Example 4. The (2S)-(−)-N-(2,3-Dihydro-7-nitro-benzo[1,4]dioxin-2-ylmethyl)-sulfamide, was then combined with 10% Pd/C in methanol (120 mL) and shaken under hydrogen atmosphere (39 psi) at room temperature for 3 h. The solids were filtered and washed with 10% M in DCM and the filtrate was evaporated in vacuo to yield crude product. The crude product was dissolved in 0.2 N HCl (25 mL), frozen and lyophilized to yield the title compound as a white flaky solid, as the corresponding hydrochloride salt.

MS (M+H)⁺ 260
¹H NMR (DMSO d6): δ 10.2 (bd s, 3H), 6.86 (m, 1H), 6.85 (s, 1H), 6.74 (dd, J=2.5, 8.4 Hz, 1H), 4.22 (m, 2H), 3.88 (dd, J=6.7, 11.4 Hz, 1H), 3.04 (m, 2H).

EXAMPLE 12

(2S)-(−)-N-(7-Methyl-2,3-dihydro-benzo[1,4]dioxin-2-ylmethyl)-sulfamide (Compound #19)

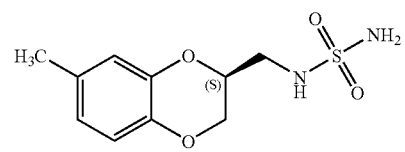

Title compound was prepared according to the procedure described in Example 4 above, starting with 4-methylcatechol, to yield a white solid, which was recrystallized from ethyl acetate/hexane to yield the title compound as a white solid.

MS [M−H]⁻ 257
¹H NMR (CDCl3): δ 6.76 (m, 1H), 6.66 (m, 2H), 4.80 (m, 1H), 4.57 (bd s, 1H), 4.40 (m, 1H), 4.28 (m, 1H), 4.03 (dd, J=6.9, 11.4 Hz, 1H), 3.45 (m, 2H), 2.25 (s, 3H).
Elemental Analysis
Calculated: C, 46.50; H, 5.46; N, 10.85; S, 12.41
Found: C, 46.65; H, 5.60; N, 10.84; S, 12.61.

EXAMPLE 13—PROPHETIC EXAMPLE

Non Randomized, Within Subject Placebo Controlled Study: Photo-Induced Paroxysnal EEG Response in Patients with Photosensitive Epilepsy Rationale for Study:

Photosensitivity offers a useful model for acute antiepileptic drug studies in man. The technique of using the photosensitive range as an index for antiepileptic action has been proven to be effective with a number of well-known antiepileptic drugs. In addition, it appears to be a useful tool for preliminary investigation of new potential antiepileptic drugs (Binnie et al., 1985; Kasteleijn-Nolst Trenité et al., 1996). Apart from information concerning the efficacy of the antiepileptic drug, the technique may, when combined with continuous blood level monitoring, also offer information concerning the time of onset and the duration of the antiepileptic action. In some cases the maximal reduction of the photosensitive range is not concurrent with, but delayed in relation to the time of the peak blood levels of a drug, as for example in the case of sodium valproate.

Using the classical photoparoxysmal response (generalised spikes, spikewaves, or polyspikewaves), as a model, the effect of the experimental antiepileptic drug on the distribution of epileptiform activity may help predict the clinical anti-convulsive spectrum of the new drug. It may lead to complete abolishment of the photoparoxysmal response, or alternatively, it may also result in the inhibition of the secondary spread and generalisation of the primary epileptiform discharges in the occipital lobe (Binnie et al., 1986).

Objective:

The objectives of the Study are as follows:

(a) to evaluate the acute antiepileptic effects of test compound (i.e. a compound of formula (I)) in photosensitive epilepsy patients, using the photoparoxysmal EEG response to intermittent photic stimulation (IPS) as a marker of antiepileptic activity; (b) to determine an oral dose of test compound (i.e. a compound of formula (I)) that results in complete suppression of photosensitivity, or reduces the photosensitivity range by at least 3 points on the photosensitivity scale in at least one eye condition (open, closure, closed); (c) to assess the relationship of the antiepileptic effect to plasma levels of test compound (i.e. a compound of formula (I)); (d) to investigate possible interactions with pre-existing antiepileptic drugs (AED); (e) to provide information on the safety and tolerability of the test compound (i.e. a compound of formula (I)) in patients with photosensitive epilepsy; and (f) to investigate the acute effect of the test compound (i.e. a compound of formula (I)) on mood in patients with photosensitive epilepsy.

Overview of the Study:

The study is a multi-center, non-randomized, single-blind, within subject placebo controlled study. All subjects receive a single dose of placebo on the morning of Day 1, a single dose of test compound (i.e. a compound of formula (I)) on the morning of Day 2 and a second single dose of placebo on the morning of Day 3. EEG tracings, recorded during IPS sessions, are printed on paper, coded and evaluated independently by 2 blinded investigators to determine the effects on the photosensitivity range.

The dose of the test compound (i.e. a compound of formula (I)) in the first three patients is selected based on animal studies. If there is a complete suppression of photosensitivity or reduction of the photosensitivity range by at least 3 points on the photosensitivity scale in at least 2 of these 3 subjects, the dose of test compound (i.e. a compound of formula (I)) is reduced in the next 3 subjects. The dose of the test compound (i.e. a compound of formula (I)) is reduced in stepwise fashion (down to a minimum dose of 250 mg) until reduction or suppression of photosensitivity is not seen, or is seen in fewer than 2 out of 3 subjects in the last dose level tested.

Once the steps above are completed, if complete suppression of photosensitivity is not seen in 2 out of the first 3 subjects at the initial dose level, the dose of the test compound (i.e. a compound of formula (I)) is increased in the next 3 subjects. The dose of the test compound (i.e. a compound of formula (I)) is increased in stepwise fashion until complete suppression of photosensitivity is seen in at least 2 subjects. These dose increases are performed only if the previous dose level is well tolerated and the new dose level is supported by safety and tolerance data from the healthy volunteer studies. In addition, these dose increases are performed only once plasma levels of the test compound (i.e. a compound of formula (I)) are known and have been compared with data from the healthy volunteer studies.

Study Population:

Up to 18 male or female subjects (3 per dose level), between 16 and 60 years of age, and with a firm diagnosis of idiopathic, photosensitive epilepsy (as characterized by a diffuse photoparoxysmal EEG response, which is not associated with mental defects or brain lesions. Subjects not using antiepileptic medication will be preferred, but use of antiepileptic medication (with the exception of felbamate) is not an exclusion criterion.

For participations in the study, each subject must satisfy the following criteria, before entering the study:

(a) aged 16 to 60 years inclusive
(b) has read and signed the informed consent form
(c) body weight between 40 and 90 kg (inclusive)
(d) firm documented diagnosis of idiopathic, photosensitive epilepsy with a diffuse photoparoxysmal EEG response
(e) consistent sensitivity to intermittent photic stimulation over a suitable range of flash frequencies
(f) no relevant abnormal clinical laboratory tests
(g) likely to be able to take part in the whole study.

Subjects who meet any of the following criteria are excluded from participating in the study:

(a) known chronic infections or allergies or history of severe allergy
(b) pregnant or lactating female or female insufficiently protected against pregnancy (for female subjects of childbearing potential, a negative pregnancy test must be obtained and either abstinence or two reliable methods of contraception must be used starting from at least 2 weeks prior to study drug administration and continuing until at least 1 week after study completion)
(c) any serious illness other than epilepsy
(d) significant neurological, psychiatric or learning disability
(e) evidence of progressive brain lesion (eg. on brain MRI or CT if appropriate)
(f) systolic blood pressure >160 or <90 mmHg and diastolic blood pressure >95 or <60 mmHg according to two repeated measures within 10 min interval
(g) regular use of non-topical medications other than current antiepileptic drugs (except felbamate) or oral contraceptives within 7 days prior to study drug administration (non-prescription OTC treatments can be accepted according to the investigator's judgement)
(h) participation in a clinical trial or use of an experimental drug within 60 days prior to study drug administration
(i) use of neuroleptics (typical or atypical), anti-depressants or Felbamate within 60 days prior to study drug administration
(j) use of more than two antiepileptic medications or change in antiepileptic medication within 30 days prior to study drug administration
(k) acute use of an antiepileptic medication within 7 days prior to study drug administration
(l) history of alcohol abuse or drug addiction within 90 days prior to study drug administration
(m) legal incapacity or limited legal capacity
(n) likely not to cooperate with or to respect the constraints of the study.

Subjects taking concomitant antiepileptic medications (with the exception of felbamate) and who are stable will continue with their regular medications maintained at the same dose level. All concomitant medication (prescription and non-prescription) will be recorded.

Dosage and Administration:

Subjects are dosed orally at approximately 09:00 hrs each day, with a standard glass of water (240 ml), under the supervision of the investigator or designated study personnel. The exact time of administration and correct intake of the capsules will be noted and recorded in the CRF.

Before any study specific procedures is conducted, the subjects reads and signs a Written Informed Consent Form.

During the screening period, within 30 days prior to study drug administration, the following assessments are completed for each subject:

(a) Medical history (including seizure history).

(b) Physical examination (including neurological examination, vital signs: standing and supine blood pressure, heart rate, weight, height and oral temperature).

(c) All medications (prescription and non-prescription), including antiepileptic drugs, used within 30 days prior to study drug administration.

(d) Full diagnostic routine EEG work-up, including control EEG and standardized determination of the photosensitivity range.

(e) 12-lead ECG.

(f) for subjects receiving concomitant antiepileptic drugs (AEDs), a blood sample for analysis of AED levels will be taken.

Standard clinical laboratory assessments include:

(a) hematology: haemoglobin, hematocrit, erythrocytes, mean corpuscular volume (MCV), mean corpuscular haemoglobin mass (MCH), mean corpuscular haemoglobin concentration (MCHC), leukocytes (total WBC and automated differential counts), platelet count.

(b) clinical chemistry: gamma glutamyl transpeptidase (γGT), alanine aminotransferase (ALT), aspartate aminotransferase (AST), alkaline phosphatase, LDH, creatinine, uric acid, glucose, total bilirubin, total protein, albumin, cholesterol, triglycerides, urea, sodium, potassium, calcium, chloride.

(c) urinalysis: glucose, protein, blood, bicarbonate, citrate, pH. If abnormal protein or blood values are found, a microscopic inspection will be performed.

Single-Blind Treatment Phase:

Subjects who have completed the screening assessments and who meet the inclusion/exclusion criteria are admitted to the hospital for the treatment phase. The duration of this treatment phase is 3 consecutive days, during which subjects are confined to the clinic for observation. Unscheduled EEG monitoring may be performed during this period at the investigator's discretion. All adverse events (AE), including seizures, are recorded between the time of first admission on Day 1 and the end of study on Day 3 (see Section 10).

On each of the three treatment days subjects are instructed to eat breakfast no later than 7:00 am (two hours before study drug administration). The breakfast should consist of a light meal (ie., dry cereal, juice, coffee/tea); fatty foods should be avoided (ie., cheese, pork, large amounts of butter/margarine, whole milk or cream). Lunch is provided at approximately 12:00, noon, and contains a balanced combination of food groups. Foods that may precipitate a hypersensitive reaction with neurological complications are avoided (ie., ergot amine containing cheeses).

Day 1: Subjects are admitted to the hospital by approximately 08:00 hrs. EEG electrodes will be put in place. For female subjects of childbearing potential a urine sample is obtained and pregnancy test performed prior to dose administration. Standard clinical laboratory assessments (as described for the screening phase) are performed within 1 hour prior to study drug administration. A single oral dose of placebo is administered at approximately 09:00 hrs. To determine the photosensitivity range, IPS and 21-channel EEG recordings are performed shortly before study drug administration and at hourly intervals up to 8 hours post-dose, following a standardized procedure. For subjects receiving concomitant antiepileptic drugs (AEDs), blood samples for analysis of AED levels are taken immediately before administration of study drug and at hourly intervals (immediately following each IPS assessment) up to 8 hours post-dose. Vital signs (standing and supine blood pressure, pulse) are recorded within 1 hour prior to study drug administration and at 1, 3, 6 and 8 hours post-dose (after photosensitivity assessments and pharmacokinetic blood sampling have been performed). A standard neurological examination is performed at 4 hours post-dose (after photosensitivity assessments and pharmacokinetic blood sampling have been performed). The POMS questionnaire wisbe administered within 1 hour prior to study drug administration and at 1, 3 and 6 hours post-dose (after photosensitivity assessments and pharmacokinetic blood sampling have been performed).

Day 2: Immediately before dosing on Day 2 subjects are instructed to void their bladders. This urine is discarded and the 10-hour urine collection period begins. All urine is collected until 10-hours post-dose. A single oral dose of test compound (i.e. a compound of formula (I)) is administered at approximately 09:00 hrs. To determine the photosensitivity range, IPS and 21-channel EEG recordings are performed shortly before study drug administration and at hourly intervals up to 8 hours post-dose, following a standardized procedure. Blood samples for analysis of test compound (i.e. a compound of formula (I)) levels are taken immediately before administration of study drug and at hourly intervals (immediately following each IPS assessment) up to 8 hours post-dose. For subjects receiving concomitant antiepileptic drugs (AEDs), blood samples for analysis of AED levels are taken immediately before administration of study drug and at hourly intervals (immediately following each IPS assessment) up to 8 hours post-dose. Vital signs (standing and supine blood pressure, pulse) are recorded within 1 hour prior to study drug administration and at 1, 3, 6 and 8 hours post-dose (after photosensitivity assessments and pharmacokinetic blood sampling have been performed). A standard neurological examination is performed at 4 hours post-dose (after photosensitivity assessments and pharmacokinetic blood sampling have been performed). The POMS questionnaire is administered within 1 hour prior to study drug administration and at 1, 3 and 6 hours post-dose (after photosensitivity assessments and pharmacokinetic blood sampling have been performed). At 10 hours post-dose the subjects are instructed to void their bladders to complete the 10-hour urine collection. The total volume of urine collected is measured and an aliquot removed for exploratory metabolite analysis.

Day 3: A single oral dose of placebo is administered at approximately 09:00 hrs. To determine the photosensitivity range, IPS and 21-channel EEG recordings is performed shortly before study drug administration and at hourly intervals up to 8 hours post-dose, following a standardized procedure. In order to examine duration of effects of test compound (i.e. a compound of formula (I)) given on Day 2, blood samples for analysis of test compound (i.e. a compound of formula (I)) levels are taken immediately before administration of the placebo dose on Day 3 and at hourly intervals (immediately following each IPS assessment) up to 8 hours post-dose on Day 3. For subjects receiving concomitant antiepileptic drugs (AEDs), blood samples for analysis of AED levels are taken immediately before administration of study drug and at hourly intervals (immediately following each IPS assessment) up to 8 hours post-dose. Vital signs (standing and supine blood pressure, pulse) are recorded within 1 hour prior to study drug administration and at 1, 3, 6 and 8 hours post-dose (after photosensitivity assessments and pharmacokinetic blood sampling have been performed). A standard neurological examination is performed at 4 hours post-dose (after photosensitivity assessments and pharmacokinetic blood sampling have been performed). The POMS questionnaire is administered within 1 hour prior to study drug administration and at 1, 3 and 6 hours post-dose (after photosensitivity assessments and pharmacokinetic blood sampling have been performed). A physical examination (including oral temperature), 12-lead ECG and standard clinical laboratory assessments (as described for the screening phase) are performed 8 hours post-dose, prior to discharge, after all previous assessments have been completed.

Posttreatment Phase (Follow-Up): Any adverse events or clinically significant laboratory abnormalities persisting at the end of the study on Day 3 are followed until resolution, or until reaching a clinically stable endpoint. If the adverse events or laboratory abnormalities can be attributed to factors other than the study drug and other than study conduct, no further follow up will be required.

Pharmocokinetic/Pharmacodynamic Evaluations:

Blood samples for assessment of plasma levels of the test compound (i.e. a compound of formula (I)) are taken immediately before administration of study drug on Day 2 and at hourly intervals (immediately following each IPS assessment) up to 8 hours post-dose. In order to examine duration of effects of the test compound (i.e. a compound of formula (I)) given on Day 2, blood samples for analysis of the test compound (i.e. a compound of formula (I)) levels are taken immediately before administration of the placebo dose on Day 3 and at hourly intervals (immediately following each IPS assessment) up to 8 hours post-dose on Day 3. For subjects receiving concomitant antiepileptic drugs (AEDs), blood samples for analysis of AED levels are taken immediately before administration of study drug and at hourly intervals (immediately following each IPS assessment) up to 8 hours post-dose on Days 1, 2 and 3. The relationship of antiepileptic effect and adverse events to plasma level, and interactions with pre-existing antiepileptic drugs are evaluated.

For determination of test compound (i.e. a compound of formula (I)) and AED concentrations, each 5-10 ml blood sample is drawn from a peripheral vein into sodium heparinized tubes and centrifuged within 15 minutes of collection for at least 15 minutes at approximately 3000 rpm in a refrigerated centrifuge. The plasma is separated into two aliquots (at least 1.2 ml each) and placed in labeled polypropylene tubes. Plasma samples are stored at −20° C. until analysis. Total volumes of the 24-hour urine collections are measured. A 250 ml sample is removed, labeled and frozen for exploratory metabolite analysis. Plasma samples are analyzed to determine concentration of test compound (i.e. a compound of formula (I)) using a validated, specific and sensitive LC-MS/MS method. Analysis of samples for determination of concomitant AED concentrations is completed by standard techniques at a central laboratory.

Plasma concentrations of test compound (i.e. a compound of formula (I)) are determined immediately before administration of study drug on day 2 and at hourly intervals (immediately following each IPS assessment) up to 8 hours post-dose. In order to examine duration of effects of test compound (i.e. a compound of formula (I)) given on Day 2, blood samples for analysis of test compound (i.e. a compound of formula (I)) levels are also taken immediately before administration placebo dose on Day 3 and at hourly intervals (immediately following each IPS assessment) up to 8 hours post-dose on Day 3. For patients receiving concomitant AEDs, AED levels will be determined from samples taken before administration of study drug and at hourly intervals (immediately following each IPS assessment) up to 8 hours post-dose on days 1, 2 and 3.

Intermittent photic stimulation (IPS) are performed to determine the photosensitivity range pre-dose and at hourly intervals up to 8 hours post-dose on days 1, 2 and 3. The IPS assessment follows a standard procedure using a Grass-type PS 22 photic stimulator with an unpatterned lamp glass at a distance from the nasion of approximately 300 mm and with an intensity of 100 cd/m$^2$/flash. Subjects are seated and instructed to fixate on the center of the lamp. Trains of flashes at constant frequency are delivered for 4-6 seconds. Intervals between the successive flash trains at a given frequency last at least 5 seconds. The following frequencies are tested: 2, 4, 8, 10, 13, 15, 18, 20, 23, 25, 30, 40, 50 and 60 Hz. First the lower limit is established by starting with 2-Hz stimulation and testing successive increasing standard frequencies (as defined above) until epileptiform activity is elicited. Then the upper sensitivity limit is defined, beginning at 60 Hz and decreasing the flash frequency in a stepwise manner until diffuse/generalized epileptiform activity is again elicited. IPS sensitivity is tested for each of three eye conditions: open, during closure, closed. A change in photosensitivity is calculated from the differences in the sensitivity range on the scale of frequencies given above (each frequency tested represents one point on the scale). For example, a change from 10 and 25 Hz (lower and upper limits) to 18 and 20 Hz would give a difference of 3+2 =5 points.

As soon as diffuse/generalized EEG epileptiform activity appears, the stimulation at the frequency in question is terminated. This procedure is performed in a hospital setting under the supervision of a qualified physician. It very rarely results in actual seizure activity. If a seizure should occur, trained and experienced medical staff is on hand to intervene as required. If any subject does experience a seizure during the IPS procedure, that subject is withdrawn from the study. IPS sessions are monitored and recorded on video.

Mood is determined using the Profile of Mood States (POMS) instrument. The POMS is a self-administered scale of general psychopathology, consisting of 65 ordinal items (Educational and Industrial Testing Service, San Diego, Calif.). In the POMS the subject checks one of the 5 degrees of each item:

0=Not at all
1=A little
2=Moderately
3=Quite a bit
4=Extremely

During the pre-study visit, the questionnaire is presented to the subject, but not completed. Explanations on the manner to complete the questionnaire are given. It usually suffices to make sure the instructions are clear and then leave the POMS with the subject to complete. The examiner is available in case questions arise. Questions are answered, but the examiner avoids defining one POMS item by referring to any other POMS item. Most subjects complete the POMS in about three-five minutes. At the end, the examiner checks that all items have been answered.

A factorial analysis isolates 6 factors:
Tension-Anxiety: items 2, 10, 16, 20, 22, 26, 27, 34, 41
Depression-Dejection: items 5, 9, 14, 18, 21, 23, 32, 35, 36, 44, 45, 48, 58, 61, 62
Anxiety-Hostility: items 3, 12, 17, 24, 31, 39, 42, 47, 52, 53, 57
Fatigue: items 4, 11, 29, 40, 46, 49, 65
Vigor: items 7, 15, 19, 38, 51, 56, 60, 63
Confusion: items 8, 28, 37, 50, 54, 59, 64
The sum of the items corresponding to each factor is calculated.

Safety Evaluations:
Standard clinical laboratory assessments (biochemistry, hematology and urinalysis) are performed at the screening visit, within 1 hour prior to study drug administration on Day 1 and 8 hours after study drug administration (prior to discharge) on Day 3. Vital signs (blood pressure and pulse) are assessed at the screening visit, within 1 hour prior to study drug administration and at 1, 3, 6 and 8 hours post-dose (after photosensitivity assessment and pharmacokinetic blood sampling have been performed) on Days 1, 2 and 3. A standard 12-lead ECG and physical examination, including oral temperature is performed at the screening visit and immediately prior to discharge on Day 3. Standard neurological examination is performed at screening and at 4 hours post-dose on Days 1, 2 and 3. Adverse events are reported between the time of first admission on Day 1 and the end of study on Day 3.

For all the subjects included in the study, demographic data (sex, age, weight height and body mass index) as well as results of $P_{450}$ genotyping and diagnostic EEG are summarised using descriptive statistics. Abnormal medical history will only be listed by subject. For physical examination and standard neurological examination all anomalies are listed. Frequency tables are computed for baseline examinations and for all changes from the baseline examination results.

Clinical laboratory, ECG and vital signs (including oral temperature) are summarised for pre-study (selection phase) and for changes from baseline to each timepoint of assessment. ECG, vital sign and laboratory values out of normal range are flagged in the listings and their frequency summarised if applicable. Shifts of laboratory values from pre-study to end of study in low/normal/high categories are summarised. Vital signs are presented graphically as individual profiles over time.

Clinical safety evaluation is based upon the review of individual values (ECG, vital signs, blood and urine analysis), values outside normal range (ECG, vital signs, blood and urine analysis) and descriptive statistics (summary tables, graphics).

Adverse Events (AEs) are reported by the subject (or where appropriate by the subject's legally authorized representative) for the duration of the study. All adverse events are coded and tabulated by body system, individual events within each body system and presented in descending frequency. Adverse events are also tabulated by severity and relationship to the study medication. Serious or potentially serious adverse events are summarised separately.

The following clinical laboratory tests are performed: (a) Hematology Panel including haemoglobin, hematocrit, erythrocytes, mean corpuscular volume (MCV), mean corpuscular haemoglobin mass (MCH), mean corpuscular haemoglobin concentration (MCHC), leukocytes (total WBC and automated differential counts), platelet count; (b) Chemistry Panel including gamma glutamyl transpeptidase ($\gamma$GT), alanine aminotransferase (ALT), aspartate aminotransferase (AST), alkaline phosphatase, LDH, creatinine, uric acid, glucose, total bilirubin, total protein, albumin, cholesterol, triglycerides, urea, sodium, potassium, calcium, chloride and (c) Urinalysis including glucose, protein, blood, bicarbonate, citrate, pH. If abnormal protein or blood values are found, a microscopic inspection will be performed. Any clinically significant abnormalities persisting at the end of the study are followed until resolution, or until reaching a clinically stable endpoint.

A subject is considered as having completed the study if he/she has completed all three study days of the treatment phase. Subjects who are withdrawn from the study for any reason before completion of this phase are not considered to have completed.

Subject participation may be terminated prior to completing the treatment phase for any of the following reasons: (a) Adverse Event; (b) Subject choice; (c) Lost to follow-up, (d) Other. When a subject withdraws prior to completing the study, the reason for withdrawal is documented on the CRFs and in the source document. Study drug assigned to the withdrawn subject is not assigned to another subject. Subjects who withdraw prior to completing all scheduled assessments on study day 2 are replaced.

Efficacy Criteria:

The photosensitivity range is evaluated from 21-channel EEG recordings made during IPS sessions performed at the screening visit, shortly before study drug administration and at hourly intervals up to 8 hours post-dose on Days 1, 2 and 3. Mood is determined using the Profile of Mood States (POMS) instrument administered within 1 hour prior to study drug administration and at 1, 3 and 6 hours post-dose (after photosensitivity assessment and pharmacokinetic blood sampling have been performed) on Days 1, 2 and 3.

Complete suppression or 3 point reduction in the IPS sensitivity range in 2 out of 3 subjects is considered valid evidence of antiepileptic activity of test compound (i.e. a compound of formula (I)) at the dose level(s) at which this occurs. Failure to find a dose level at which either of the above criteria is met in at least one eye condition (open, closure, closed) is interpreted as insufficient effectiveness of the drug.

Efficacy Evaluations [Pharmacodynamics]:

The main objective of the study is to evaluate the acute antiepileptic effect of test compound (i.e. a compound of formula (I)). A secondary objective is to investigate the effect of test compound (i.e. a compound of formula (I)) on mood.

The statistical analysis of antiepileptic effect is based on the photosensitivity ranges provided by the 2 blinded investigators based on the EEG tracings, recorded during the IPS sessions. The photosensitivity ranges is expressed as lower and upper IPS-frequency limits (Hz) for each timepoint of assessment, and will be evaluated statistically as follows. Profiles of the photosensitivity ranges over all 3 study days are plotted for each individual. Individual percentage changes of the photosensitivity range area from dosing to 8 hours post-dose on day 2 as compared with the corresponding area of Day 1 are described. Individual percentage changes of the mean photosensitivity range post-dose of Day 2 from the photosensitivity range pre-dose of Day 2 are summarized. If for an individual a decrease in the photosensitivity range from pre-dose to post-dose of Day 2 of at least 3 points on the frequency scale (see Section 9.3) is observed then the reaction of this subject is interpreted as positive. These results are used for decision of dose changes in the dose finding procedure.

For the analysis of the secondary objective, mood, 6 factor scores is calculated as detailed in 9.3, Efficacy Evaluations: tension-anxiety, depression-dejection, anxiety-hostility, fatigue, vigor and confusion score. The results are shown as individual profiles of each factor over time.

Pharmacokinetic/Pharmacodynamic Analyses:

Two objectives are of interest, relationship of the antiepileptic effect to plasma levels, and interactions with pre-existing antiepileptic drugs. Both objectives are examined based on graphs showing profiles of plasma levels of test compound (i.e. a compound of formula (I)) and of eventual concomitant AEDs together with photosensitivity ranges over all 3 study days, one graph per subject.

The relation between change in photosensitivity range and test compound (i.e. a compound of formula (I)) plasma level are described as onset time, amount and duration of the antiepileptic reaction in relation to the time of the estimated peak blood level. Onset time of any antiepileptic reaction is where the change of the interpolated profile range reaches 50% of its maximal change. The duration is interpreted to end where the profile range again widens to more than 50% of its maximal change. The amount of the reaction is taken as the individual percentage change of the mean photosensitivity range post-dose of Day 2 from the photosensitivity range pre-dose of Day 2.

If any patients with concomitant AEDs are participating in the study, their graphs are compared with the graphs of non-AED patients, and sensitivity profiles and AEs for the two groups described to investigate any pharmacokinetic interactions.

EXAMPLE 14

As a specific embodiment of an oral composition, 100 mg of the Compound #8 prepared as in Example 7 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A method for treating epilepsy comprising administering to a subject in need thereof, co-therapy with a therapeutically effective amount of one or more anti-epileptic or anti-convulsant agents and a therapeutically effective amount of compound of formula (I)

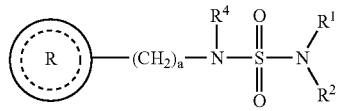

wherein
R¹ and R² are each independently selected from the group consisting of hydrogen and lower alkyl;
R⁴ is selected from the group consisting of hydrogen and lower alkyl;
a is an integer from 1 to 2;

is selected from the group consisting of

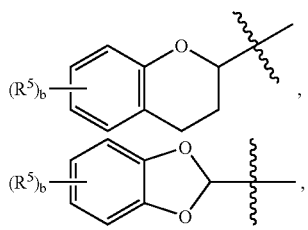

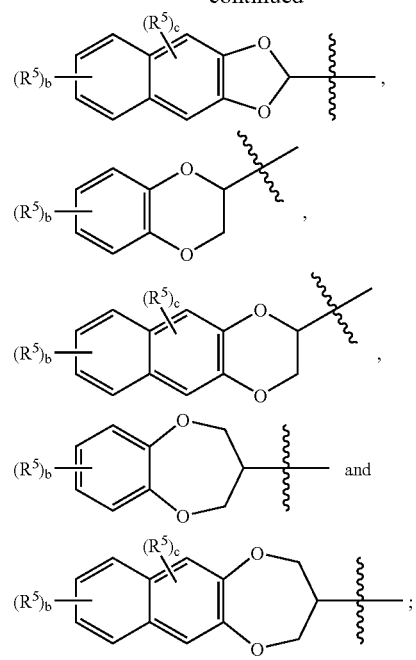

wherein b is an integer from 0 to 4; and wherein c is an integer from 0 to 2;
each R⁵ is independently selected from the group consisting of halogen and lower alkyl;
provided that when

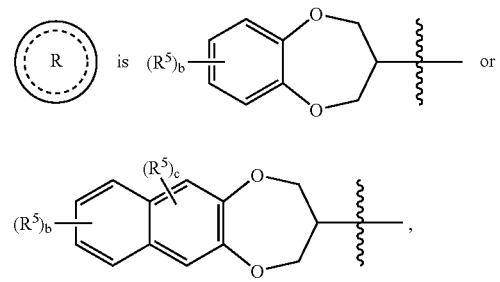

then a is 1;
or a pharmaceutically acceptable salt thereof.
2. The method as in claim 1, wherein
R¹ and R² are each independently selected from the group consisting of hydrogen and lower alkyl;
R⁴ is selected from the group consisting of hydrogen and lower alkyl;
a is an integer from 1 to 2;

is selected from the group consisting of

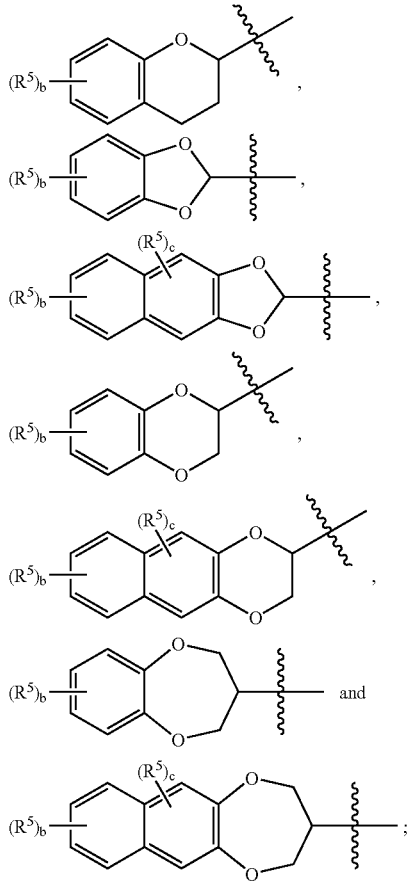

wherein b is an integer from 0 to 2; and wherein c is an integer from 0 to 1;
each $R^5$ is independently selected from the group consisting of halogen, lower alkyl and nitro;
provided that when

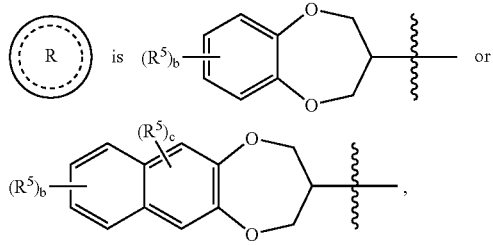

then a is 1;
or a pharmaceutically acceptable salt thereof.

3. The method as in claim 2, wherein
$R^1$ and $R^2$ are each independently selected from the group consisting of hydrogen and lower alkyl;
$R^4$ is selected from the group consisting of hydrogen and lower alkyl;
a is an integer from 1 to 2;

is selected from the group consisting of

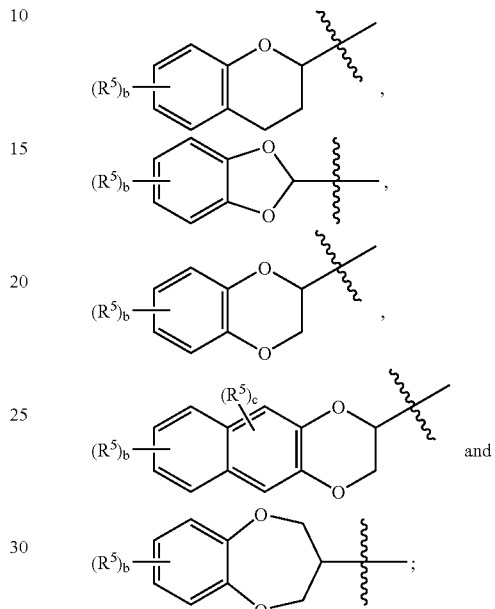

wherein b is an integer from 0 to 2; and wherein c is 0;
each $R^5$ is independently selected from the group consisting of halogen, lower alkyl and nitro;
provided that when

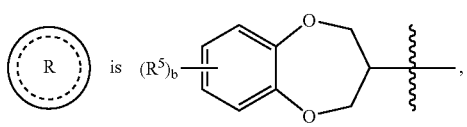

then a is 1;
or a pharmaceutically acceptable salt thereof.

4. The method as in claim 3, wherein
$R^1$ and $R^2$ are each independently selected from the group consisting of hydrogen and lower alkyl;
$R^4$ is selected from the group consisting of hydrogen and methyl;
a is an integer from 1 to 2;

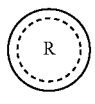

is selected from the group consisting of 2-(2,3-dihydro-benzo[1,4]dioxinyl), 2-(benzo[1,3]dioxolyl), 2-(3,4-dihydro-2H-benzo[1,4]dioxepinyl), 2-(2,3-dihydro-benzo[1,4]dioxinyl), 2-(6-chloro-2,3-dihydro-benzo[1,4]dioxinyl), 2-(6-fluoro-2,3-dihydro-benzo [1,4] dioxinyl), 2-(chromanyl), 2-(5-fluoro-2,3-dihydrobenzo [1,4]dioxinyl), 2-(7-chloro-2,3-dihydro-benzo[1,4]dioxinyl), 2-(6-chloro-benzo [1,3]dioxolyl), 2-(7-nitro-2,3-dihydro-benzo[1,4]dioxinyl), 2-(7-methyl-2,3-dihydro-benzo [1,4]dioxinyl), 2-(5-chloro-2,3-dihydro-benzo[1,4]dioxinyl), 2-(6-bromo-2,3-dihydro-benzo [1,4]dioxinyl), 2-(6,7-dichloro-2,3-dihydro-benzo[1,4]dioxinyl), 2-(8-chloro-2,3-dihydro-benzo[1,4]dioxinyl), 2-(2,3-dihydro-naphtho[2,3-b][1,4]dioxinyl) and 2-(4-methyl-benzo [1,3]dioxolyl);

provided that when

is 2-(3,4-dihydro-2H-benzo[1,4]dioxepinyl), then a is 1;

or a pharmaceutically acceptable salt thereof.

5. The method as in claim 4, wherein
$R^1$ and $R^2$ are each independently selected from the group consisting of hydrogen and methyl;
$R^4$ is selected from the group consisting of hydrogen and methyl;
a is an integer from 1 to 2;

is selected from the group consisting of 2-(benzo[1,3]dioxolyl), 2-(2,3-dihydro-benzo [1,4]dioxinyl), 2-(2,3-dihydro-benzo[1,4]dioxinyl), 2-(6-chloro-2,3-dihydro-benzo [1,4]dioxinyl), 2-(7-chloro-2,3-dihydro-benzo[1,4]dioxinyl), 2-(7-methyl-2,3dihydro-benzo[1,4]dioxinyl), 2-(6-bromo-2,3-dihydro-benzo[1,4]dioxinyl) and 2-(6,7dichloro-2,3-dihydro-benzo[1,4]dioxinyl);

or a pharmaceutically acceptable salt thereof.

6. The method of claim 1, wherein the compound of formula (I) is selected from the group consisting of (2S)-(−)-N-(6-chloro-2,3-dihydro-benzo[1,4]dioxin-2-ylmethyl)-sulfamide; and pharmaceutically acceptable salts thereof.

7. A method for treating epilepsy or a related disorder, comprising administering to a subject in need thereof, cotherapy with a therapeutically effective amount of one or more anti-epileptic or anti-convulsant agents and a therapeutically effective amount of (2S)-(−)-N-(6-chloro-2,3-dihydro-benzo[1,4]dioxin-2ylmethyl)-sulfamide or a pharmaceutically acceptable salt thereof.

8. The method of claim 1, wherein the anti-convulsant or anti-epileptic agent is selected from the group consisting of carbamazepine, clobazam, clonazepam, ethosuximide, felbamate, gabapentin, lamotrigine, levetiracetam, oxcarbazepine, phenobarbital, phenytoin, pregabalin, primidone, retigabine, rufinamide, talampanel, tiagabine, topiramate, valproate, vigabatrin, zonisamide, benzodiazepines, barbiturates and sedative hypnotics.

9. The method of claim 8, wherein the anti-convulsant or anti-epileptic agent is selected from the group consisting of carbamazepine, clobazam, clonazepam, ethosuximide, felbamate, gabapentin, lamotrigine, levetiracetam, oxcarbazepine, phenobarbital, phenytoin, pregabalin, primidone, retigabine, rufinamide, talampanel, tiagabine, topiramate, valproate, vigabatrin and zonisamide.

10. The method of claim 9, wherein the anti-convulsant or anti-epileptic agent is selected from the group consisting of carbamazepine, gabapentin, lamotrigine, levetiracetam, oxcarbazepine, phenytoin, pregabalin, valproate and topiramate.

11. The method of claim 7, wherein the anti-convulsant or anti-epileptic agent is selected from the group consisting of carbamazepine, clobazam, clonazepam, ethosuximide, felbamate, gabapentin, lamotrigine, levetiracetam, oxcarbazepine, phenobarbital, phenytoin, pregabalin, primidone, retigabine, rufinamide, talampanel, tiagabine, topiramate, valproate, vigabatrin, zonisamide, benzodiazepines, barbiturates and sedative hypnotics.

12. The method of claim 11, wherein the anti-convulsant or anti-epileptic agent is selected from the group consisting of carbamazepine, clobazam, clonazepam, ethosuximide, felbamate, gabapentin, lamotrigine, levetiracetam, oxcarbazepine, phenobarbital, phenytoin, pregabalin, primidone, retigabine, rufinamide, talampanel, tiagabine, topiramate, valproate, vigabatrin and zonisamide.

13. The method of claim 12, wherein the anti-convulsant or anti-epileptic agent is selected from the group consisting of carbamazepine, gabapentin, lamotrigine, levetiracetam, oxcarbazepine, phenytoin, pregabalin, valproate and topiramate.

14. A method for the treatment of epilepsy comprising administering to a subject in need thereof, co-therapy with a therapeutically effective amount of one or more anticonvulsant or anti-epileptic agents and a therapeutically effective amount of a compound of formula

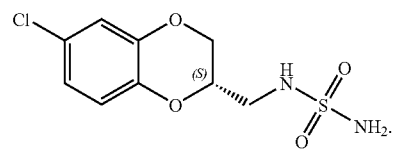

15. The method of claim 14, wherein the anti-convulsant or anti-epileptic agent is selected from the group consisting of carbamazepine, clobazam, clonazepam, ethosuximide, felbamate, gabapentin, lamotrigine, levetiracetam, oxcarbazepine, phenobarbital, phenytoin, pregabalin, primidone, retigabine, rufinamide, talampanel, tiagabine, topiramate, valproate, vigabatrin, zonisamide, benzodiazepines, barbiturates and sedative hypnotics.

16. The method of claim 15, wherein the anti-convulsant or anti-epileptic agent is selected from the group consisting of carbamazepine, clobazam, clonazepam, ethosuximide, felbamate, gabapentin, lamotrigine, levetiracetam, oxcarbazepine, phenobarbital, phenytoin, pregabalin, primidone, retigabine, rufinamide, talampanel, tiagabine, topiramate, valproate, vigabatrin and zonisamide.

17. The method of claim 16, wherein the anti-convulsant or anti-epileptic agent is selected from the group consisting of carbamazepine, gabapentin, lamotrigine, levetiracetam, oxcarbazepine, phenytoin, pregabalin, valproate and topiramate.

* * * * *